(12) United States Patent
Baughman et al.

(10) Patent No.: US 7,176,310 B1
(45) Date of Patent: Feb. 13, 2007

(54) PYRIMIDINECARBOXAMIDE DERIVATIVES AND THEIR USE AS ANTI-INFLAMMATORY AGENTS

(75) Inventors: Theodore A. Baughman, Bothell, WA (US); Jim P. Boyce, Kirkland, WA (US); Ihab S. Darwish, Seattle, WA (US); J. Jeffry Howbert, Bellevue, WA (US); Nathan C. Ihle, Mercer Island, WA (US); Randy W. Jackson, Snohomish, WA (US); Scott C. Jeffrey, Everett, WA (US); Dean Maeda, Bothell, WA (US); Kraig M. Yager, Snohomish, WA (US)

(73) Assignee: UCB SA, Slough (GB)

( * ) Notice: Subject to any disclaimer, the term of this patent is extended or adjusted under 35 U.S.C. 154(b) by 156 days.

(21) Appl. No.: 10/407,870

(22) Filed: Apr. 4, 2003

Related U.S. Application Data

(60) Provisional application No. 60/371,265, filed on Apr. 9, 2002.

(51) Int. Cl.
*C07D 239/00* (2006.01)
*C07D 239/70* (2006.01)

(52) U.S. Cl. ............ 544/253; 544/243; 544/245; 544/246; 544/247; 544/249; 544/294; 544/295

(58) Field of Classification Search ........ 544/253, 544/243, 245, 246, 247, 249, 294, 295, 254, 544/255, 322, 323, 334, 300
See application file for complete search history.

(56) References Cited

U.S. PATENT DOCUMENTS

| | | | |
|---|---|---|---|
| 3,821,225 A | 6/1974 | Regnier et al. ........ 260/268 H |
| 3,845,055 A | 10/1974 | Hoegerle et al. .... 260/256.4 N |
| 3,970,661 A | 7/1976 | Regnier et al. .......... 260/295.5 |
| 3,970,663 A | 7/1976 | Regnier et al. .......... 260/295.5 |
| 4,285,946 A * | 8/1981 | Kampe et al. ............. 514/275 |
| 4,410,530 A | 10/1983 | Frei et al. .................... 424/251 |
| 4,705,792 A | 11/1987 | Granzer et al. ............. 514/275 |
| 4,734,418 A * | 3/1988 | Yokoyama et al. .... 514/252.16 |
| 5,654,307 A | 8/1997 | Bridges et al. ............. 514/258 |
| 5,665,724 A * | 9/1997 | Sanfilippo et al. ......... 514/256 |
| 5,756,524 A * | 5/1998 | Riordan et al. ............. 514/346 |
| 5,939,424 A | 8/1999 | Böger et al. ................ 514/275 |
| 6,432,963 B1 * | 8/2002 | Hisamichi et al. ......... 514/256 |
| 6,656,935 B2 * | 12/2003 | Yamada et al. .......... 514/230.5 |
| 6,759,412 B2 * | 7/2004 | Strobel et al. ........... 514/235.5 |
| 2003/0032647 A1 | 2/2003 | Yamada et al. ........ 514/255.05 |

FOREIGN PATENT DOCUMENTS

| | | |
|---|---|---|
| DE | 2405930 | 8/1975 |
| DE | EP 0 569 912 A1 * | 11/1993 |
| EP | 0 569 912 A1 * | 11/1993 |
| EP | 0 626 428 B1 | 10/2000 |
| EP | 1 223 170 A1 | 7/2002 |
| EP | 1 277 741 A1 * | 1/2003 |
| GB | 1131784 | 10/1968 |
| JP | 49076886 | 7/1974 |
| JP | 61087672 | 5/1986 |
| JP | 01117882 | 5/1989 |
| JP | 03127790 | 5/1991 |
| JP | WO 01/021615 | 3/2001 |
| WO | WO 95/19774 | 7/1995 |
| WO | WO 95/25723 * | 9/1995 |
| WO | WO 99/06035 | 2/1999 |
| WO | WO 99/06046 | 2/1999 |
| WO | WO 99/61444 | 12/1999 |
| WO | WO 99/66925 | 12/1999 |
| WO | WO 00/39101 | 7/2000 |
| WO | WO 01/21597 | 3/2001 |

(Continued)

OTHER PUBLICATIONS

Kosegi et al., "Preparation of N-(1H-Tetrazol-5-yl)-2-anilino-5-pyrimidinecarboxamide Derivatives as Antiallergic and Antiulcer Agents", *Chemical Abstracts Database*, Accession No. 1991:583346, 1989. Abstract corresponds to entry BM below.

(Continued)

*Primary Examiner*—James O. Wilson
*Assistant Examiner*—Chukwuma Nwaonicha
(74) *Attorney, Agent, or Firm*—Jane E. R. Potter; Kerry Fluhr; Davis Wright Tremaine LLP

(57) ABSTRACT

This invention is directed to compound of the following formula (I):

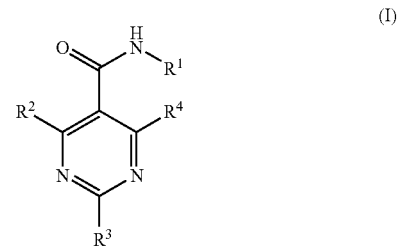

wherein $R^1$, $R^2$, $R^3$ and $R^4$ are as described herein. These compounds and pharmaceutical compositions containing the compounds are useful in treating inflammatory disorders in mammals.

11 Claims, No Drawings

FOREIGN PATENT DOCUMENTS

| WO | WO 01/44213 | 6/2001 |
|----|----|----|
| WO | WO 01/74788 | 10/2001 |
| WO | WO 02/04429 | 1/2002 |
| WO | WO 02/066036 A1 * | 8/2002 |

OTHER PUBLICATIONS

"(Amidoethyl)piperazines," *Chemical Abstracts Database*, Accession No. 1976:463091, 1972. Corresponds to entry BO above.

Regnier, et al., "N-Amidoethyl Piperazines," *Chemical Abstracts Database*, Accession No. 1976:446755, 1976.

Kon et al., "Preparation of Heterocyclic Carboxamides as Digestive Tract Motility Stimulants," *Chemical Abstracts Database*, Accession No. 1989:632842. Corresponds to entry BQ above.

Shimizu et al., "High-performance Affinity Beads for Identifying Drug Receptors", *Nature Biotechnology* (Aug. 2000), vol. 18, pp. 877-881.

Sheikh, S. P. et al., "Binding of Monoiodinated Neuropeptide Y to Hippocampal Membranes and Human Neuroblastoma Cell Lines", *The Journal of Biological Chemistry* (Apr. 29, 1989), vol. 264, pp. 6648-6654.

Fuhlendorff, J. et al., "[Leu$^{31}$,Pro$^{34}$]Neuropeptide Y: A Specific Y$_1$ Receptor Agonist", *Proceedings of the National Academy of Sciences USA* (Jan. 1990), vol. 87, pp. 182-186.

Samson, M. et al., "The Second Extracellular Loop of CCR5 Is the Major Determinant of Ligand Specificity", *The Journal of Biological Chemistry* (Oct. 3, 1997), vol. 272, pp. 24934-24941.

Ahuja, S. K. et al., "The CXC Chemokines Growth-regulated Oncogene (GRO) α, GROβ, GROγ, Neutrophil-activating Peptide-2, and Epithelial Cell-derived Neutrophil-activating Peptide-78 Are Potent Agonists for the Type B, but Not the Type A, Human Interleukin-8 Receptor", *The Journal of Biological Chemistry* (Aug. 1996), vol. 271, pp. 20545-20550.

Frei et al., "Heterocyclic compounds", *Chemical Abstracts Database*, Accession No. 1974:535967, 1974. Abstract corresponds to entry BK above.

Urleb, U. et al., "Transformations of 2,4,5-Trisubstituted Pyrimidines. The Syntheses and Transformations of Pyrimido/4,5-d/Pyrimidine, 1,2,4-Triazolo/4,3-a/Pyrimidine, Tetrazolo/1,5-a/Pyrimidine, 1,2,4-Triazolo/3,4-bPurine and Tetrazolo/5,1-b/Purine Derivatives", *Heterocycles* (1986), vol. 24, pp. 1899-1909.

Kim, D. H., "Reactions of Ethyl 4-Chloro-5-pyrimidinecarboxylates with 2-Aminopyridine. Synthesis of 5H-Pyrido[1,2-a]pyrimido[5,4-e]pyrimidin-5-ones and 5H-Pyrido[1,2-a]pyrimido[4,5-d]pyrimidin-5-ones and Rearrangement of the Former to the Latter", *Journal of Heterocyclic Chemistry* (Jan./Feb. 1985), vol. 22, pp. 173-176.

Huettinger, M. et al., "Hypolipidemic Activity of HOE-402 Is Mediated by Stimulation of the LDL Receptor Pathway", *Arteriosclerosis and Thrombosis* (1993), vol. 13, pp. 1005-1012.

Hoffman, A. et al., "Cholesterol Lowering Action of HOE 402 in the Normolipidemic and Hypercholesterolemic Golden Syrian Hamster", *Biochimica et Biophysica Acta* (1996), vol. 1299, pp. 95-102.

Gupta, S.P., "Potential Anticancer Agents: Synthesis of Cytidine-5-carboxylic Acid and Cytosine-5-carbonylaminoacids", *Indian Journal of Chemistry*, (1976), vol. 15B, pp. 463-465.

Rosania, G. R., "Myoserverin, A Microtubule-binding Molecule with Novel Cellular Effects", *Nature Biotechnology* (2000), vol. 18, pp. 304-308.

Fleming, S. A., "Chemical Reagents in Photoaffinity Labeling", *Tetrahedron* (1995), vol. 51, pp. 12479-12520.

Srikant, C. B., "Relationship between Receptor Binding and Biopotency of Somatostatin-14 and Somatostatin-28 in Mouse Pituitary Tumor Cells", *Endocrinology* (Jul. 1985), vol. 117, pp. 271-278.

Katsuragi, T. et al., "Affinity Chromatography of Cytosine Deaminase from *Escherichia coli* with Immobilized Pyrimidine Compounds", *Agricultural and Biological Chemistry* (Jul. 1986), vol. 50, pp. 1713-1719.

Thermos, K. et al., "Somatostatin Receptor Subtypes in the Clonal Anterior Pituitary Cell Lines AtT-20 and GH3", *Molecular Pharmacology* (Apr. 1988), vol. 33, pp. 370-377.

Takayama, et al., "Preparation of Benzimidazole Derivatives as Poly(ADP-ribose) Polymerase (PARP) Inhibitors", *Chemical Abstracts Database*, Accession No. 2001: 228885, 2000. Abstract corresponds to entry BP above.

Stogryn, E. L., "Synthesis of Trimethoprim Variations. Replacement of CH$_2$ by Polar Groupings", *Journal of Medicinal Chemistry* (1972), vol. 15, pp. 200-201.

Kamath, S. et al., "Calculation of Relative Binding Free Energy Difference of DHFR Inhibitors by a Finite Difference Thermodynamic Integration (FDTI) Approach", *Journal of Biomolecular Structure & Dynamics* (1999), vol. 16, pp. 1239-1244.

Dostert, R. et al., "Studies On the Neuroleptic Benzamides", *European Journal of Medicinal Chemistry—Chimie Thérapeutique* (1982), vol. 17, pp. 437-444.

Hirota, K. et al., "Novel Ring Transformations of 5-Cyanouracils into 2-Thiocytosines, 2,4-Diaminopyrimidines, and Pyrimido[4,5-d]pyrimidines by the Reaction with Thioureas and Guanidines", *Journal of the Chemical Society, Perkin Transactions I* (1990), vol. 1, pp. 123-128.

Karlsson, R. et al., "Biosenser Analysis of Drug-Target Interactions: Direct and Competitive Binding Assays for Investigation of Interactions Between Thrombin and Thrombin Inhibitors", *Analytical Biochemistry* (2000), vol. 278, pp. 1-13.

Kampe, K. D., "2-Cyano-3-ethoxyacrylamides—Selective Reactive Synthons for Synthesis of Heterocyclics", abstract provided from *Chemical Abstracts Database*, Accession No. 1982:509955. See also *Angewandte Chemie* (1982), vol. 94, pp. 543-544.

Regnier, G. L., "Bronchodilator Substances. I. Synthesis and Structure-activity Relationships Between New Benzoic and Heterocyclic Amide Derivatives", abstract provided from *Chemical Abstracts Database*, Accession No. 1975:112035. See also *Arzneimittel-Forschung* (1974), vol. 24, pp. 1964-1970.

Hoffman, A. et al., "Cholesterol Lowering Potency of HOE 402 in the Hypercholesterolemic Golden Syrian Hamster", *Adv. Lipoprotein Atheroscler. Res. Diagn, Treat., Proc. Int. Dresden Lipid Symp.*, 8$^{th}$ (1995), Meeting Date 1994, pp. 255-257; Eds. Jaross, Werner; Publisher: Fischer, Jena, Germany.

Gulevskaya, A. et al., "Purines, Pyrimidines and Condensed Systems Based On Them. 12. 1,3-Dimethylpyrimido[4,5-d]pyrimidine-2,4(1H,3H)-dione: The First Case of Regioselective Amination of Condensed Pyrimidines at Position 2", abstract provided from *Chemical Abstracts Database*, Accession No. 1995:334056. See also *Khim. Geterotsikl, Soedin.* (1994), vol. 9, pp. 1249-1252.

Dozorova, E. N. et al., "Acetals of Lactams and Acid Amides. 56. Pyrimidine Derivatives from N-carbamoyl amidines", abstract provided from *Chemical Abstracts Database*, Accession No. 1990:478316. See also *Khim. Geterotsikl. Soedin.* (1990), vol. 1, pp. 81-84.

Mishio, S. et al., "Studies on Ampicillin and Amoxicillin Derivatives. III. Synthesis of 6-[2-[(Pyrido[2,3-d]pyrimidin-6-yl)methylamino]-2-phenylacetamido]penicillanic Acid Derivatives, and -cephalosporanic Acid Derivatives", abstract provided from *Chemical Abstracts Database*, Accession No. 1988:186366. See also *Yagugaku Zasshi* (1987), vol. 107, pp. 607-615.

Hirota, K. et al., "Novel Synthesis of 2-Thiocytosine Derivatives via Pyrimidine-to-Pyrimidine Ring Transformation", *Heterocycles* (1984), vol. 22, pp. 2259-2262.

Frevert, C. W., "Rapid Fluorescence-based Measurements of Neutrophil Migration in vitro", *Journal of Immunological Methods* (1998), vol. 213, pp. 41-52.

* cited by examiner

PYRIMIDINECARBOXAMIDE DERIVATIVES AND THEIR USE AS ANTI-INFLAMMATORY AGENTS

CROSS-REFERENCE TO RELATED APPLICATION

This application claims the benefit of U.S. Provisional Patent Application No. 60/371,265 filed Apr. 9, 2002, where this provisional application is incorporated herein by reference in its entirety.

FIELD OF THE INVENTION

This invention is directed to pyrimidinecarboxamide derivatives and their use as anti-inflammatory agents. This invention is also directed to pharmaceutical compositions containing the derivatives, processes for making the derivatives and methods of using the derivatives to treat inflammatory disorders in mammals, particularly in humans.

BACKGROUND OF THE INVENTION

Chemotactic cytokines (chemokines) are a class of potent inflammatory mediators that have the potential to attract specific subsets of leukocytes to sites of inflammation. Chemokines are typically low molecular mass (7–9 kD) proteins that can be divided into four subfamilies based on their primary amino acid structure. The CXC subfamily is characterized by the two conserved Cys (C) residues near the N-terminus, which are separated by an amino acid (X). Some of the CXC chemokines, such as IL-8 and growth related oncogene alpha (GRO-α), belong further to the ELR+ subfamily (Glu-Leu-Arg) and are important in the recruitment and activation of neutrophils.

The interaction of chemokines with specific cell populations is mediated by G-protein-coupled seven-transmembrane receptors (7TMR). Chemokine receptors can be classified into four groups (CR, CCR, CXCR, CX3CR) based upon their primary amino acid sequence. The CXCR1 receptor binds with high affinity to interleukin 8 (IL-8) and low affinity to NAP-2, ENA-78 (epithelial cell-derived neutrophil-activating factor), GRO-α, GRO-β and GRO-γ, whereas CXCR2 binds with high affinity to all of the afore-mentioned CXC chemokines. Both CXCR1 and CXCR2 receptors are found primarily on neutrophils and a subset of T-cells. See, e.g., Holmes, W., et al., Science (1991), Vol. 253, p. 1278; Murphy, P., et al., Science (1991), Vol. 253, p. 1280; Chuntharapai, A., et al., J. Immunol. (1994), Vol. 153, p. 5682; and Xu, L., et al., J. Leukocyte Biol. (1995), Vol. 57, p. 335. High levels of IL-8 and tissue neutrophil infiltration have been observed in the synovial tissues of rheumatoid arthritis patients (Endo, H., Lymphokine Cytokine Res.(1991), Vol. 10, p. 245). Evidence has been presented that GRO-α and IL-8 are important mediators involved in the recruitment of neutrophils in the early and late phase of lipopolysaccharide-induced (LPS) rabbit arthritis (Matsukawa, A, et al. Lab. Invest. (1991), Vol. 79, p. 591). The murine CXCR2 receptor has also shown to be necessary for neutrophilic inflammation in a mouse model of gouty synovitis (Terkeltaub, R., et al., Arthriti. Rheum. (1998), Vol. 41, p. 900. 41:900)

CXC chemokines have attracted attention as being important in the development of atherosclerosis (Terkeltaub, R., et al., Curr. Opin. Lipido.l(1998), Vol. 9, p. 937). The role of CXCR1 and CXCR2 ligands on monocyte function in atherosclerosis in rabbits was published by Schwartz, D., et al., J. Clin. Invest. (1994), Vol. 94, p. 1968. Knockout mice that lacked CXCR2 expression had diminished lesion size (Boisvert, W., et al., J. Clin. Invest. (1998), Vol. 101, p. 353).

The involvement of the CXCR2 receptor in the pathological inflammatory response elicited by central nervous system (CNS) cells as related to Alzheimer's disease is also gaining significant attention (Xia, M., et al., J. Neurovirol. (1999), Vol. 5, p. 32). Reports have focused on the upregulation of CXCR2 expression on dystrophic neurites of senile plaques. See, e.g., Xia, M., et al., Am. J. Pathol. (1997), Vol. 150, p. 1267, and Horuk, R., et al., J. Immunol. (1997), Vol. 158, p. 2882.

High levels of IL-8 and neutrophil infiltration have been observed in the pathogenesis of a number of other disease indications. This includes ulcerative colitis (Mahida, Y., et al., Clin. Sci. (1992), Vol. 82, p. 273, and Izzo, R., Am. J. Gastroenterol. (1992), Vol. 87, p. 1447) and psoriasis (Gillitzer, R., et al., J. Invest. Dermatol. (1996), Vol. 107, p. 778 and Kojima, T., J. Invest. Dermatol. (1993), Vol. 101, p. 767). CXCR1 and CXCR2 chemokines and their roles in tumor growth and metastasis have been reviewed. See, e.g., Wang, J., J. Immunol. Meth. (1998), Vol. 220, p. 1.

To date, a limited number of CXCR1 and CXCR2 receptor antagonists have been reported. It was reported that a bis-aryl urea was able to selectively inhibit CXCR2 receptor and prevent neutrophil margination and chemotaxis in a rabbit model. See, e.g., White, J., J. Biol. Chem. (1998), Vol. 273, p. 10095. Other CXCR1 and CXCR2 receptor antagonists have focused on $NH_2$-terminal truncations and modifications of IL-8, GRO-α, and ELR motif (Jones, S., et al., J. Biol. Chem., Vol. 272, p. 16166). Murine neutrophil recruitment in vivo could also be inhibited via CXCR2 receptor blocking using a truncated human GRO-αanalog. There are currently no CXCR1 or CXCR2 receptor antagonist based therapies widely available.

There is a continued need for the treatment of diseases mediated by the CXCR2 receptor. Small molecule antagonists of the CXCR2 receptor and their ligands, such as GRO-α and IL-8, would be useful in the control of harmful inflammatory processes as well as important tools for the investigation of receptor-ligand interactions.

SUMMARY OF THE INVENTION

This invention is directed to pyrimidinecarboxamide derivatives and their use in treating inflammatory disorders in mammals, particularly in humans. These derivatives are CXCR2 receptor antagonists. In particular, the derivatives are useful for the prophylaxis and treatment of diseases or conditions involving inflammation due to neutrophil chemotaxis mediated via the CXCR2 receptor. This invention also relates to intermediates and processes useful in the preparation of such derivatives.

Accordingly, in one aspect, this invention provides compounds of formula (Ia):

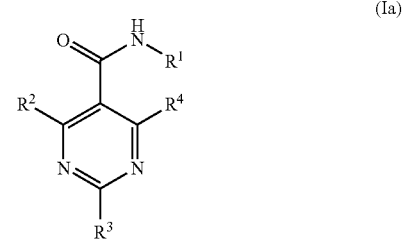

(Ia)

wherein, independently at each occurrence:

$R^1$ is selected from aralkyl and aryl;

$R^2$ is selected from hydrogen and $-N(R^5)R^6$;

$R^3$ is selected from —O—$R^7$ and —S(O)$_t$—$R^7$ where t is 0 to 2;
$R^4$ is selected from hydrogen, halo, and alkyl;
$R^5$ is selected from hydrogen and alkyl;
$R^6$ is selected from hydrogen, alkyl, haloalkyl, carbocyclyl, aryl, aralkyl, heteroalkyl, heterocyclyl, and heterocyclylalkyl; or
$R^5$ and $R^6$, together with the nitrogen to which they are attached, form a heterocyclyl; and
$R^7$ is selected from alkyl, aryl, aralkyl, heteroalkyl, heterocyclyl and heterocyclylalkyl;
provided, however, that $R^1$ can not be phenyl substituted at the 2-position by carboxy or alkoxycarbonyl when $R^2$ and $R^4$ are both hydrogen and $R^3$ is —O—$R^7$ where $R^7$ is methyl, ethyl, pyridinyl, or 4-methoxyphenyl, or when $R^2$ and $R^4$ are both hydrogen and $R^3$ is —S—$R^7$ where $R^7$ is methyl or pyridinyl, or when $R^2$ and $R^4$ are both hydrogen and $R^3$ is —S(O)—$R^7$ or —S(O)$_2$—$R^7$ where $R^7$ is methyl;
as a single stereoisomer, a mixture of individual stereoisomers, or a racemic mixture;
or a pharmaceutically acceptable salt thereof.

In another aspect, this invention is directed to compounds of formula (Ib):

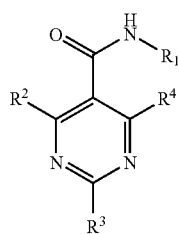

(Ib)

wherein, independently at each occurrence:
$R^1$ is selected from aralkyl and aryl each substituted by one or more substituents selected from halo, haloalkyl, and haloalkoxy;
$R^2$ is selected from hydrogen and —N($R^5$)$R^6$;
$R^3$ is —N($R^{10}$)$R^{11}$;
$R^4$ is selected from hydrogen, halo and alkyl;
$R^5$ is selected from hydrogen and alkyl;
$R^6$ is selected from hydrogen, alkyl, haloalkyl, carbocyclyl, aryl, aralkyl, heteroalkyl, heterocyclyl and heterocyclylalkyl; or
$R^5$ and $R^6$, together with the nitrogen to which they are attached, form a heterocyclyl;
$R^{10}$ is selected from hydrogen and alkyl; and
$R^{11}$ is selected from alkyl, aryl, aralkyl, carbocyclyl, carbocyclylalkyl, and heteroalkyl; or
$R^{10}$ and $R^{11}$, together with the nitrogen to which they are attached, form a heterocyclyl, provided that such heterocyclyl is not imidazolin-2-onyl or 4-phenylpiperazinyl;
as a single stereoisomer, a mixture of individual stereoisomers, or a racemic mixture; or
pharmaceutically acceptable salts or solvates thereof.

In another aspect, this invention is directed to pharmaceutical compositions useful in treating an inflammatory disorder in a mammal, particularly a human, wherein the composition comprises one or more pharmaceutically acceptable excipient(s) and a therapeutically effective amount of a compound of formula (Ia) as described above.

In another aspect, this invention is directed to pharmaceutical compositions useful in treating an inflammatory disorder in a mammal, particularly a human, wherein the composition comprises one or more pharmaceutically acceptable excipient(s) and a therapeutically effective amount of a compound of formula (Ib) as described above.

In another aspect, this invention is directed to methods of treating an inflammatory disorder in a mammal, particularly a human, wherein the method comprises administering to the mammal in need thereof a therapeutically effective amount of a compound of formula (I):

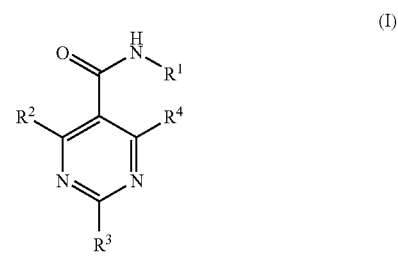

(I)

wherein, independently at each occurrence:
$R^1$ is selected from aralkyl and aryl;
$R^2$ is selected from hydrogen and —N($R^5$)$R^6$;
$R^3$ is selected from —N($R^{10}$)$R^{11}$, —O—$R^7$ and —S(O)$^t$—$R^7$ where t is 0 to 2;
$R^4$ is selected from hydrogen, halo, and alkyl;
$R^5$ is selected from hydrogen and alkyl;
$R^6$ is selected from hydrogen, alkyl, haloalkyl, carbocyclyl, aryl, aralkyl, heteroalkyl, heterocyclyl, and heterocyclylalkyl; or
$R^5$ and $R^6$, together with the nitrogen to which they are attached, form a heterocyclyl;
$R^7$ is selected from alkyl, aryl, aralkyl, heteroalkyl, heterocyclyl and heterocyclylalkyl;
$R^{10}$ is selected from hydrogen and alkyl; and
$R^{11}$ is selected from alkyl, aryl, aralkyl, carbocyclyl, carbocyclylalkyl, and heteroalkyl; or
$R^{10}$ and $R^{11}$, together with the nitrogen to which they are attached, form a heterocyclyl;
as a single stereoisomer, a mixture of individual stereoisomers, or a racemic mixture; or
pharmaceutically acceptable salts or solvates thereof.

In another aspect, this invention is directed to methods of treating an inflammatory disorder in a mammal alleviated by the inhibition of a CXCR2 receptor, wherein the method comprises administering to the mammal in need thereof a compound of formula (I) as described above in an amount effective to inhibit the CXCR2 receptor.

In another aspect, this invention is directed to methods for inhibiting a G-protein-coupled seven-transmembrane domain (7TM) receptor in a mammal, wherein the method comprises administering to the mammal in need thereof a compound of formula (I) as described above in an amount effective to inhibit the receptor.

In another aspect, this invention is directed to methods for inhibiting a chemokine-mediated cellular event, wherein the method comprises administering to a mammal in need thereof a compound of formula (I) as described above in an amount effective to inhibit the chemokine-mediated cellular event.

In another aspect, this invention is directed to methods for identifying a binding partner to a compound of formula (I)

as described above, wherein the method comprises immobilizing proteins known to be involved in the chemokine signaling pathway onto a suitable carrier; and passing a solution of said compounds in isolation or mixture over said proteins and analyzing for compound-protein complex formation using surface plasmon resonance (SPR).

In another aspect, this invention is directed to methods for identifying a binding partner to a compound of formula (I) as described above, wherein the method comprises providing the compound bound to a solid support to provide a solid phase compound; contacting a cell or cell components comprising the binding partner with the solid phase compound in isolation or mixture; removing uncomplexed cellular material, and recovering said binding partner from the solid phase compounds.

In another aspect, this invention is directed to methods for identifying a binding partner to a compound of formula (I) as described above, wherein the method comprises contacting a cell or cell component comprising a binding partner with said compound in isolation or mixture; providing a means for covalent attachment of the compound to said binding partner to form a compound:binding partner complex; isolating the compound:binding partner complex from said cell or cell component; and isolating and identifying the binding partner from the compound:binding partner complex.

These and other related aspects of the present invention are set forth in more detail below.

DETAILED DESCRIPTION OF THE INVENTION

Definitions

As used in the specification and appended claims, unless specified to the contrary, the following terms have the meaning indicated:

Unless otherwise indicated, the term "a" refers to one, or more than one, of the indicated items. For example, "a compound" includes both one, and more than one, compound.

"Alkyl" is a saturated or unsaturated, straight or branched, hydrocarbon chain. In various embodiments, the alkyl group has 1–18 carbon atoms, i.e., is a C1–C18 group, or is a C1–C12 group, a C1–C6 group, or a C1–C4 group. A lower alkyl group has 1–6 carbons. Independently, in various embodiments, the alkyl group has zero branches (i.e., is a straight chain), one branch, two branches, or more than two branches. Independently, in one embodiment, the alkyl group is saturated. In another embodiment, the alkyl group is unsaturated. In various embodiments, the unsaturated alkyl may have one double bond, two double bonds, more than two double bonds, and/or one triple bond, two triple bonds, or more than two triple bonds. Alkyl chains may be optionally substituted with 1 substituent (i.e., the alkyl group is monosubstituted), or 1–2 substituents, or 1–3 substituents, or 1–4 substituents, etc. The substituents may be selected from the group consisting of hydroxy, amino, alkylamino, carboxy, nitro, cyano, and the like. When the alkyl group incorporates one or more heteroatoms, the alkyl group is referred to herein as a heteroalkyl group. When the substituents on an alkyl group are hydrocarbons, then the resulting group is simply referred to as a substituted alkyl. In various aspects, the alkyl group including substituents has less than 25, 24, 23, 22, 21, 20, 19, 18, 17, 16, 15, 14, 13, 12, 11, 10, 9, 8, or 7 carbons.

"Aralkyl" refers to an alkyl group as defined substituted by one or more aryl groups as defined below. Phenyl and naphthyl are preferred aryl groups in an aralkyl group. A preferred alkyl group is methyl, so that a preferred aralkyl group is benzyl or benzyl having one or more substituents on the phenyl ring. Unless other indicated, the term "aralkyl" as used herein is meant to include aralkyl groups wherein the aryl ring therein is optionally substituted by one or more substituents selected from acyl (—C(O)—R), alkoxy (—OR), alkyl, aryl, alkylamino (—N(H)R and —N(R)R), alkylthio (—S—R), amino (—NH$_2$), azido (—N$_3$), carboxy (—C(O)OH), alkoxycarbonyl (—C(O)OR), aminocarbonyl (—C(O)NH$_2$), aminosulfonyl (—S(O)$_2$—NH$_2$), alkylaminocarbonyl (—C(O)N(H)R and —C(O)N(R)R), cyano (—CN), halo (fluoro, bromo, chloro, iodo), haloalkyl, haloalkoxy, heterocyclyl, heteroalkyl, hydroxy (—OH), mercapto (—SH) and nitro (—NO$_2$) where each R is an alkyl group having less than about 12 carbons, preferably where the R group is a lower alkyl group. In addition, the alkyl group of the aralkyl group may also be optionally substituted by one or more substituents selected from hydroxy, amino, carboxy, alkoxycarbonyl and the like.

"Aryl" is an aromatic carbocyclic hydrocarbon ring system. The ring system may be monocyclic or fused polycyclic (e.g., bicyclic, tricyclic, etc.). In one embodiment, the aryl group is monocyclic, and is preferably a C6 ring system, i.e., a phenyl ring is a preferred aryl ring. In another embodiment aryl group is a bicyclic aryl ring, where preferred bicyclic aryl rings are C8–C12, or C9–C10. A naphthyl ring, which has 10 carbon atoms, is a preferred polycyclic aryl ring. Unless otherwise indicated herein, the term "aryl" as used herein is meant to include aryl rings optionally substituted by one or more substituents selected from acyl (—C(O)—R), alkoxy (—O—R), alkyl, aryl, alkylamino (—N(H)R and —N(R)R), alkylthio (—S—R), amino (—NH$_2$), azido (—N$_3$), carboxy (—C(O)OH), alkoxycarbonyl (—C(O)OR), aminocarbonyl (—C(O)NH$_2$), aminosulfonyl (—S(O)$_2$ —NH$_2$), alkylaminocarbonyl —C(O)N(H)R and —C(O)N(R)R), cyano (—CN), halo (fluoro, bromo, chloro, iodo), haloalkyl, heteroalkyl, hydroxy (—OH), mercapto (—SH) and nitro (—NO$_2$) where each R is an alkyl group having less than about 12 carbons, preferably where the R group is a lower alkyl group.

"Carbocyclyl", also referred to herein as carbocyclic aliphatic ring, is a saturated or unsaturated, monocyclic or polycyclic (e.g., bicyclic, tricyclic, etc.) non-aromatic hydrocarbon ring substituent. A polycyclic carbocyclyl substituent may include fused, spiro or bridged ring structures. In various embodiments, the monocyclic carbocyclyl substituent is a C3–C10, or a C4–C7, or a C5–C6 ring system. In various embodiments, the polycyclic carbocyclyl substituent is a C6-C12, or a C9-C10 ring system. In one embodiment, the polycyclic carbocyclyl is bicyclic. In another embodiment, the polycyclic carbocyclyl is bicyclic or tricyclic. Carbocyclyl substituents include cyclopropyl, cyclopentyl, cyclohexyl, cyclohexenyl, cycloheptyl, and cyclooctyl. Carbocyclyl substituents may be substituted or unsubstituted. In one embodiment, the carbocyclyl is unsubstituted. In another embodiment, the carbocyclyl is substituted with, e.g., 1 substituent (i.e., the alkyl group is monosubstituted), or 1–2 substituents, or 1–3 substituents, or 1–4 substituents, etc. In one embodiment, the substituents that may be present on the carbocyclic aliphatic ring are selected from acyl (—C(O)—R), alkoxy (—O—R), alkyl, alkylamino (—N(H)R and —N(R)R), alkylthio (—S—R), amino (—NH$_2$), azido (—N$_3$), carboxy (—C(O)OH), alkoxycarbonyl (—C(O)OR), aminocarbonyl (—C(O)NH$_2$), alkylaminocarbonyl (—C(O)N(H)R and —C(O)N(R)R), cyano (—CN), halo, heterocyclyl, heteroalkyl, hydroxy (—OH), mercapto (—SH) and nitro (—NO₂). In one aspect, the R group in the above substituents is an alkyl group having less than about 12 carbons, while in another aspect the R group is a lower alkyl group.

"Carbocyclylalkyl" is an alkyl or heteroalkyl group having a carbocyclyl substituent as defined above in lieu of one of the alkyl or heteroalkyl group's hydrogen atoms. The carbocyclyl in the carbocyclylalkyl substituent may be substituted as described above.

"Commercially available chemicals" and the chemicals used in the Examples set forth herein may be obtained from standard commercial sources, where such sources include, for example, Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.),Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hannover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

"Compound", as in the terms "compound of the formula", "compound of the structure", "compound of the invention", and the like, shall refer to and encompass the chemical compound itself as well as, whether explicitly stated or not, and unless the context makes clear that one or more of the following is to be excluded: amorphous and crystalline forms of the compound, including polymorphic forms, where these forms may be part of a mixture or in isolation; free acid and free base forms of the compound, which are typically the forms shown in the structures provided herein; isomers of the compound, which refers to optical isomers and tautomeric isomers, where optical isomers include enantiomers and diastereomers, chiral isomers and non-chiral isomers, and the optical isomers include isolated optical isomers as well as mixtures of optical isomers including racemic and non-racemic mixtures; where an isomer may be in isolated form or in admixture with one or more other isomers; isotopes of the compound, including deuterium- and tritium-containing compounds, and including compounds containing radioisotopes, including therapeutically- and diagnostically-effective radioisotopes; multimeric forms of the compound, including dimeric, trimeric, etc. forms; salts of the compound, preferably pharmaceutically acceptable salts, including acid addition salts and base addition salts, including salts having organic counterions and inorganic counterions, and including zwitterionic forms, where if a compound is associated with two or more counterions, the two or more counterions may be the same or different; and solvates of the compound, including hemisolvates, monosolvates, disolvates, etc., including organic solvates and inorganic solvates, said inorganic solvates including hydrates; where if a compound is associated with two or more solvent molecules, the two or more solvent molecules may be the same or different. In some instances, reference made herein to a compound of the invention will include an explicit reference to one or of the above forms, e.g., salts and solvates, however, this reference is for emphasis only, and is not to be construed as excluding other forms as identified above.

"Compounds described in the chemical literature" may be identified though reference books and databases directed to chemical compounds and chemical reactions, as known to one of ordinary skill in the art. Suitable reference books and treatise that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., www.acs.org may be contacted for more details). Chemicals that are known but not commercially available in catalogs may be prepared by custom chemical synthesis houses, where many of the standard chemical supply houses (e.g., those listed above) provide custom synthesis services.

"Halo" refers to fluoro, bromo, iodo or chloro.

"Haloalkyl" is an alkyl group as defined above substituted by one or more halo atoms. Examples include 2-chloroethyl and trifluoromethyl.

"Haloalkoxy" is —O-haloalkyl where haloalkyl is as defined above.

"Heteroatom" is a nitrogen, sulfur, oxygen or silicon atom. Groups containing more than one heteroatom may contain different heteroatoms.

"Heteroalkyl" is a saturated or unsaturated, straight or branched, chain containing carbon and at least one heteroatom. The heteroalkyl group may, in various embodiments, have one heteroatom, or 1–2 heteroatoms, or 1–3 heteroatoms, or 1–4 heteroatoms. In one aspect the heteroalkyl chain contains from 1 to 18 (i.e., 1–18) member atoms (carbon and heteroatoms) in the chain, and in various embodiments contain 1–12, or 1–6, or 1–4 member atoms. Independently, in various embodiments, the heteroalkyl group has zero branches (i.e., is a straight chain), one branch, two branches, or more than two branches. Independently, in one embodiment, the heteroalkyl group is saturated. In another embodiment, the heteroalkyl group is unsaturated. In various embodiments, the unsaturated heteroalkyl may have one double bond, two double bonds, more than two double bonds, and/or one triple bond, two triple bonds, or more than two triple bonds. Heteroalkyl chains may be substituted or unsubstituted. In one embodiment, the heteroalkyl chain is unsubstituted. In another embodiment, the heteroalkyl chain is substituted. A substituted heteroalkyl chain may have 1 substituent (i.e., be monosubstituted), or may have 1–2 substituents, or 1–3 substituents, or 1–4 substituents, etc. Exemplary heteroalkyl groups include esters (—C(O)—OR) and carbonyls (—C(O)—).

"Heterocyclyl" to a stable 3- to 15-membered ring radical which consists of carbon atoms and from one to five heteroatoms. For purposes of this invention, the heterocyclyl radical may be a monocyclic, bicyclic or tricyclic ring system, which may include fused or bridged ring systems; and any nitrogen, carbon or sulfur atoms present in the heterocyclyl ring may be optionally oxidized; any nitrogen atoms may be optionally quaternized; and the heterocyclyl radical may be aromatic or partially or fully saturated. The heterocyclyl radical may be attached to the main structure at any heteroatom or carbon atom which results in the creation of a stable compound. Examples of such heterocyclyl radicals include, but are not limited to, azepinyl, acridinyl, benzimidazolyl, benzthiazolyl, benzoxazolyl, benzopyranyl, benzopyranonyl, benzofuranyl, benzofuranonyl, benzothienyl, carbazolyl, cinnolinyl, decahydroisoquinolyl, dioxolanyl, furanyl, furanonyl, isothiazolyl, imidazolyl, imidazolinyl, imidazolidinyl, isothiazolidinyl, indolyl, isoindolyl, indolinyl, isoindolinyl, indolizinyl, isoxazolyl, isoxazolidinyl, morpholinyl, naphthyridinyl, oxadiazolyl, octahydroindolyl, octahydroisoindolyl, 2-oxopiperazinyl, 2-oxopiperidinyl, 2-oxopyrrolidinyl, 2-oxoazepinyl, oxazolyl, oxazolidinyl, oxiranyl, piperidinyl, piperazinyl, 4-piperidonyl, phenazinyl, phenothiazinyl, phenoxazinyl, phthalazinyl, pteridinyl, purinyl, pyrrolyl, pyrrolidinyl, pyrazolyl, pyrazolidinyl, pyridinyl, pyrazinyl, pyrimidinyl, pyridazinyl, quinazolinyl, quinoxalinyl, quinolinyl, quinuclidinyl, isoquinolinyl, thiazolyl, thiazolidinyl, thiadiazolyl, triazolyl, tetrazolyl, tetrahydrofuryl, triazinyl, tetrahydropyranyl, thienyl, thiamorpholinyl, thiamorpholinyl sulfoxide, and thiamorpholinyl sulfone. In one embodiment, the heterocyclyl ring is a N-heterocyclyl, i.e., the heterocyclyl ring contains at least one nitrogen atom. The heterocyclyl may be unsubstituted or substituted. In one embodiment, the heterocyclyl is unsubstituted. In another embodiment, the heterocyclyl is substituted. The substituted heterocyclyl ring may contain 1 substituent, or 1–2 substituents, or 1–3 substituents, or 1–4 substituents, etc. In one embodiment, the substituents that may be present on the heterocyclyl ring are selected from acyl (—C(O)—R), alkoxy (—O—R), alkyl, aryl, alkylamino (—N(H)R and —N(R)R), alkylthio (—S—R), amino (—NH$_2$), azido (—N$_3$), carboxy (—C(O)OH), alkoxycarbonyl (—C(O)OR), aminocarbonyl (—C(O)NH$_2$), alkylaminocarbonyl (—C(O)N(H)R and —C(O)N(R)R), cyano (—CN), halo, heteroalkyl, hydroxy (—OH), mercapto (—SH) and nitro (—NO$_2$). In one aspect, the R group which is, or is part of the substituent attached to the heteroaryl ring is an alkyl group having less than about 12 carbons, while in another aspect the R group is a lower alkyl group.

"Heterocyclylalkyl" is an alkyl group as defined above substituted by one or more heterocyclyl groups as defined above.

"Independently at each location", "independently at each occurrence", and the like mean that any selection is independent of any other selection. For instance, if a variable is selected from two options, and the variable occurs twice, then the option selected at one occurrence of the variable does not impact in any way the choice of the option selected at the second occurrence of the variable.

"Mammal" includes humans and domesticated animals, such as cats, dogs, swine, cattle, sheep, goats, horses, rabbits, and the like.

As used herein, "methods known to one of ordinary skill in the art" may be identified though various reference books and databases. Suitable reference books and treatise that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., www.acs.org may be contacted for more details). Chemicals that are known but not commercially available in catalogs may be prepared by custom chemical synthesis houses, where many of the standard chemical supply houses (e.g., those listed above) provide custom synthesis services.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt", "salts thereof", and the like refer to organic or inorganic salts of the referenced pharmaceutically important molecule. The salts are formed from one or more of the pharmaceutically important referenced molecules and one or more counterions as needed to stabilizes the charge(s) on the pharmaceutically important molecule(s). A pharmaceutically acceptable salt may involve the inclusion of another molecule, such as an acetate ion, a succinate ion or other counterion. Furthermore, a pharmaceutically important organic molecule may have more than one charged atom in its structure. Situations where multiple charged atoms are part of the molecule may have multiple counterions. Hence, the molecule of a pharmaceutically acceptable salt may contain one, or more than one, charged atoms and may also contain one, or more than one, counterion. The desired charge distribution is determined according to methods of drug administration. Examples of pharmaceutically acceptable salts are well known in the art but, without limiting the scope of the present invention, exemplary presentations can be found in the Physician's Desk Reference, The Merck Index, The Pharmacopoeia and Goodman & Gilman's The Pharmacological Basis of Therapeutics. The salt will typically be either an acid addition salt, i.e., a salt formed by adding an acid to a pyrimidine compound of the invention, or a base addition salt, i.e., a salt formed by adding a base to a pyrimidine compound of the invention. The pyrimidine compounds of the invention may contain at least one amine group, for example, $R^2$ may be an amine group, and accordingly acid addition salts may be formed with this amine group, where acid addition salts refer to those salts which retain the biological effectiveness and properties of the free base and which are not biologically or otherwise undesirable, formed with inorganic acids such as hydrochloric acid, hydrobromic acid, sulfuric acid, nitric acid, phosphoric acid and the like, or organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. The possible substituents on an aryl group include carboxylic acid, and accordingly base addition salts may be formed with this (or any other) carboxylic acid group, where base addition salts refer to those salts which retain the biological effectiveness and properties of the free acid and which are not biologically or otherwise undesirable, formed with inorganic bases such as ammonia or organic bases such as alkylamines.

"Pharmaceutically acceptable solvate" refers to a solvate that retains the biological effectiveness and properties of the biologically active pyrimidine compound of the invention. Examples of pharmaceutically acceptable solvates include, but are not limited to, water, isopropanol, ethanol, methanol, DMSO, ethyl acetate, acetic acid, and ethanolamine. It will be appreciated by those skilled in the art that solvated forms are biologically equivalent to unsolvated forms and are intended to be encompassed within the scope of the present invention. Sykes, P. A., Guidebook to Mechanism in Organic Chemistry, 6th Ed (1986, John Wiley & Sons, N.Y.) is an exemplary reference that describe solvates.

"Pharmaceutically acceptable excipient" as used herein is intended to include without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, emulsifier, or stabilizer which has been approved by the United States Food and Drug Administration as being acceptable for use in humans or domestic animals.

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7–9, 21–24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol and amine functional groups in the compounds of the invention and the like.

As used herein, "suitable conditions" for carrying out a synthetic step are explicitly provided herein or may be discerned by reference to publications directed to methods used in synthetic organic chemistry. The reference books and treatise set forth above that detail the synthesis of reactants useful in the preparation of compounds of the present invention, will also provide suitable conditions for carrying out a synthetic step according to the present invention.

"Stable compound" and "stable structure" are meant to indicate a compound that is sufficiently robust to survive isolation to a useful degree of purity from a reaction mixture, and formulation into an efficacious therapeutic agent.

"Therapeutically effective amount" refers to that amount of a compound of the invention which, when administered to a mammal, particularly a human, in need thereof, is sufficient to effect treatment, as defined below, for and inflammatory disorder in the human. The amount of a compound of the invention which constitutes a "therapeutically effective amount" will vary depending on the compound, the inflammatory disorder and its severity, and the age of the mammal to be treated, but can be determined routinely by one of ordinary skill in the art having regard to his own knowledge and to this disclosure.

"Treating" or "treatment" as used herein covers the treatment of an inflammatory disorder in a mammal, preferably a human, and includes:

(i) preventing the disorder from occurring in a mammal, in particular, when such mammal is predisposed to the disorder but has not yet been diagnosed as having it;

(ii) inhibiting the disorder, i.e., arresting its development; or (iii) relieving the disorder, i.e., causing regression of the disorder or inflammation.

The compounds of the invention, or their pharmaceutically acceptable salts, may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as, their racemic and optically pure forms. Optically active (R)- and (S)-, or (D)- and (L)- isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

The nomenclature used herein is a modified form of the I.U.P.A.C. nomenclature system wherein the compounds of the invention are named herein as derivatives of the pyrimidinecarboxamide moiety. Thus, a compound of formula (Ia) wherein $R^1$ is 4-fluorophenyl, $R^2$ is hydrogen, $R^3$ is methylthio and $R^4$ is hydrogen, i.e., a compound of the following formula:

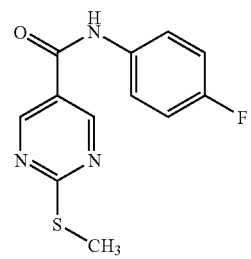

is named herein as 2-methylsulfanylpyrimidine-5-carboxylic acid (4-fluorophenyl)amide.

The use of parentheses in a formula herein is used to conserve space. Accordingly, the use of parenthesis in a formula indicates that the group enclosed within the parentheses is attached directly to the atom preceding the parenthesis. For example, —$(CH_2)_n$—$C(O)N(R^8)R^9$ where n is 2 can be drawn as follows:

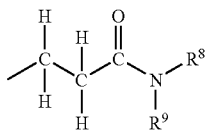

Unless otherwise indicated by the nomenclature, compound names are intended to include any single stereoisomer, enantiomer, racemate or mixtures thereof.

Utility and Testing of the Compounds of the Invention

The present invention provides pyrimidinecarboxamide derivatives, pharmaceutical compositions containing the derivatives and methods of using the derivatives to inhibit chemokine-mediated cellular events involving the CXCR2 receptor. Thus, in one aspect, the present invention provides a method to modulate binding of IL-8 and GRO-α to cell receptors, and/or modulate the consequential intracellular events comprising administering to a mammal, preferably a human, in a need thereof a therapeutically effective amount of a compound of formula (I) as described above in the Summary of the Invention. Thus, in one aspect, the present invention provides a method for the inhibition of chemokines binding to the CXCR2 receptor comprising administering an amount of a compound of formula (I) effective to inhibit said binding. In another aspect, the present invention provides a method for treating, preventing, or treating and/or preventing one or more of inflammatory and autoimmune diseases such as Inflammatory Bowel Disease (IBD), psoriasis, rheumatoid arthritis, Acute Respiratory Distress Syndrome (ARDS), cancer, atherosclerosis, reperfusion injury, and graft vs. host disease, comprising administering to a subject in need thereof an effective amount of a compound of formula (I).

In another aspect, the present invention provides a method of using the compounds of formula (I) and pharmaceutical compositions containing a compound of formula (I) to inhibit G-protein-coupled, seven-transmembrane domain (7TM) receptors. Thus, in one aspect, the present invention provides a method to modulate the binding of MIP-1β to CCR5 cell receptors. In another aspect, the present invention provides a method to modulate the binding of Peptide YY (PYY) to NPY cell receptors. In another aspect, the present invention provides a method to modulate the binding of somatostatin to somatostatin cell receptors. In one aspect, the compound of formula (I) modulates the binding by reducing the effective binding of MIP-1β to cell receptor.

The present invention also provides a method for treating an inflammatory disorder in a mammal, preferably a human, wherein the method comprises administering to a mammal in need thereof, through a therapeutically or prophylactically acceptable manner, a therapeutically or pharmaceutically effective amount of the compound of formula (I). Administration may be selected from transdermal, oral, intravenous, intramuscular, vaginal, rectal, pulmonary, subcutaneous, sublingual and transmucosal administration.

In another aspect, the present invention provides a method for identifying a binding partner to a compound of formula (I) as set forth above in the Summary of the Invention, where the method comprises: immobilizing a protein known to be involved in the chemokine signaling pathway onto a suitable carrier; and passing a solution of said compound in isolation or mixture over said protein and analyzing for compound: protein complex formation using surface plasmon resonance (SPR). This method may be performed in analogy to the method described in Karlsson, R., et al., "Biosensor Analysis of Drug-Target Interactions: Direct and Competitive Binding Assays for Investigation of Interactions Between Thrombin and Thrombin Inhibitors", Anal. Biochem. (2000), Vol. 278, No. 1, pp. 1–13. For other examples of identifying small molecule-protein interactions using SPR see the Biacore website: http://www.biacore.com.

In another aspect, the present invention provides a method for identifying a binding partner to a compound of formula (I) as set forth above in the Summary of the Invention, where the method comprises: contacting a cell or cell components containing a binding partner with said compound in isolation or mixture; removing uncomplexed cellular material, for example by gentle washing with aqueous buffer; and recovering said binding partner from the compound. The compound(s) of formula (I) are preferably bound to a solid support See, e.g., methodology reported in Shimizu, N., et al., "High Performance Affinity Beads for Identifying Drug Receptors", Nature Biotechnology (2000), Vol. 18, No. 8, pp. 877–881.

The above-described utilities of the compounds of formula (I) may be determined by a variety of in vitro and in vivo assays known to one of ordinary skill in the art. For example, GRO-α driven chemotaxis assays may be performed in a manner similar to that which is disclosed in Frevert, et al., J. Immunol. Meth. (1998), Vol. 213, pp. 41–52. The binding of [$^{125}$I]IL-8 to human CXCR2 receptor may be performed in a manner similar to the method disclosed in Ahuja, S. K., et al., J. Biol. Chem. (1996), Vol. 271, pp. 20545–20550. The binding of [$^{125}$I]MIP-1β to human chemokine CXCR5 receptor may be performed in a manner similar to the method disclosed in Samson, M., et al., J. Biol. Chem. (1997), Vol. 272, pp. 24934–24941. The binding of [$^{125}$I]Peptide YY (PYY) to human neuropeptide $Y_1$ ($NPY_1$) receptors may be performed in a manner similar to the method disclosed in Fuhlendorff, J., et al., Proc. Natl. Acad. Sci. USA (1990), Vol. 87, pp. 182–186, and Sheikh, S. P., et al., J. Biol. Chem. (1989), Vol. 264, pp. 6648–6654. The binding of [$^{125}$I]tyr$^1$ somatostatin to somatostatin receptors may be performed in a manner similar to the method disclosed in Thermos, K., et al., Mol. Pharmacol. (1988), Vol. 33, pp. 370–377, and Srikant, C. B., et al, Endocrinology (1985), Vol. 117, pp. 271–278.

In another aspect, the present invention provides a method for identifying a binding partner to a compound of formula (I) as disclosed herein, where the method comprises contacting a cell or cell component comprising a binding partner with said compound in isolation or mixture; providing a means for covalent attachment of the compound to said binding partner to form a compound:binding partner complex; isolating the compound:binding partner complex from said cell or cell component; and isolating and identifying the binding partner from the compound:binding partner complex. The means for the covalent attachment of the compound to the binding partner may be accomplished using photolysis (see for example Steve A. Fleming, "Chemical Reagents in Photoaffinity Labeling", *Tetrahedron* (1995), Vol. 51, No. 46, pp. 12479–12520), through a direct alkylation step (see for example Gustavo R. Rosinia, et al., "Myoseverin, a microtubule-binding molecule with novel cellular effect", *Nature Biotechnology* (2000), Vol. 18, pp. 304–308), or by other means known to one skilled in the art. The isolation of the compound:binding partner complex or the isolation of the binding partner from the compound: binding partner complex may be accomplished through gel electrophoresis and autoradiography, affinity purification, or other techniques known to one skilled in the art. The identification of the binding partner may be based on protein sequence analysis, tryptic digest with mass spec analysis, or other methods known to one skilled in the art.

All references cited throughout this disclosure are incorporated in full by reference herein.

Administration of the Compounds of the Invention

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the present invention may be in any form that allows for the composition to be administered to a patient. Typical routes of administration include, without limitation, oral, topical, transdermal, inhalation, parenteral, sublingual, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state characterized by inflammation in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, e.g., inhalatory administration.

When intended for oral administration, the composition is preferably in either solid or liquid form, where semi-solid, semi-liquid, suspension and gel forms are included within the forms considered herein as either solid or liquid.

As a solid composition for oral administration, the composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the composition is in the form of a capsule, e.g., a gelatin capsule, it may contain, in addition to materials of the above type, a liquid carrier such as polyethylene glycol or a fatty oil.

The composition may be in the form of a liquid, e.g., an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid composition intended for either parenteral or oral administration should contain an amount of the inventive compound such that a suitable dosage will be obtained. Typically, this amount is at least 0.01% of a compound of the invention in the composition. When intended for oral administration, this amount may be varied to be between 0.1 and about 70% of the weight of the composition. Preferred oral compositions contain between about 4% and about 50% of the compound of the invention. Preferred compositions and preparations according to the present invention are prepared so that a parenteral dosage unit contains between 0.01 to 1% by weight of the compound of the invention.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

The pharmaceutical composition may be intended for rectal administration, in the form, e.g., of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the present invention may consist of dosage units which can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient (s). Delivery of the aerosol includes the necessary container, activators, valves, subcontainers, and the like, which together may form a kit. One skilled in the art, without undue experimentation may determine preferred aerosols. Whether in solid, liquid or gaseous form, the pharmaceutical composition of the present invention may contain one or more known pharmacological agents used in the treatment of inflammation.

The pharmaceutical compositions may be prepared by methodology well known in the pharmaceutical art. For example, a composition intended to be administered by injection can be prepared by combining a compound of the invention with water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disease-state; and the host undergoing therapy. Generally, a therapeutically effective daily dose is from about 0.14 mg to about 14.3 mg/kg of body weight per day of a compound of the invention, or a pharmaceutically acceptable salt thereof; preferably, from about 0.7 mg to about 10 mg/kg of body weight per day; and most preferably, from about 1.4 mg to about 7.2 mg/kg of body weight per day. For example, for administration to a 70 kg person, the dosage range would be from about 10 mg to about 1.0 gram per day of a compound of the invention, or a pharmaceutically acceptable salt thereof, preferably from about 50 mg to about 700 mg per day, and most preferably from about 100 mg to about 500 mg per day.

Preferred Embodiments

Of the compounds of the invention as set forth above in the Summary of the Invention, several groups of compounds are particularly preferred.

Accordingly, a preferred group of compounds of formula (Ia) as set forth above in the Summary of the Invention is that group of compounds wherein $R^2$ is hydrogen.

Of this preferred group, a preferred subgroup is that subgroup of compounds wherein $R^1$ is aryl.

Of this preferred subgroup, a preferred class is that class of compounds wherein $R^1$ is phenyl substituted with one or more substituents selected from acyl, alkoxy, alkyl, alkylamino, alkylthio, amino, azido, carboxy, alkoxycarbonyl, aminocarbonyl, alkylaminocarbonyl, cyano, halo, heteroalkyl, hydroxy, mercapto and nitro.

Another preferred class is that class of compounds wherein $R^1$ is phenyl substituted with one or more substituents selected from azido, $C_1$–$C_{10}$alkyl, and halo.

Another preferred group of compounds of formula (Ia) is that group of compounds wherein $R^2$ is —$N(R^5)R^6$ and each of $R^5$ and $R^6$ is hydrogen.

Of this preferred group, a preferred subgroup is that subgroup of compounds wherein $R^1$ is aralkyl.

Of this preferred subgroup, a preferred class is that class of compounds wherein $R^1$ is benzyl and the phenyl group of the benzyl is substituted with one or more substituents selected from acyl, alkyl, alkoxy, alkylamino, alkylthio, amino, azido, carboxy, alkoxycarbonyl, aminocarbonyl, alkylaminocarbonyl, cyano, halo, heteroalkyl, hydroxy, mercapto and nitro.

Of this preferred class, a preferred subclass is that subclass of compounds wherein $R^1$ is benzyl and the phenyl group of the benzyl is substituted with one or more fluoro substituents.

Another preferred subgroup is that subgroup of compounds wherein $R^1$ is aryl.

Of this preferred subgroup, a preferred class is that class of compounds wherein $R^1$ is phenyl optionally substituted with one or more substituents selected from acyl, alkoxy, alkyl, alkylamino, alkylthio, amino, azido, carboxy, alkoxycarbonyl, aminocarbonyl, alkylaminocarbonyl, cyano, halo, heteroalkyl, hydroxy, mercapto and nitro.

Another preferred class is that class of compounds wherein $R^1$ is phenyl optionally substituted with one or more substituents selected from acyl, alkoxy, alkyl, alkylamino, alkylthio, amino, azido, cyano, halo, heteroalkyl, hydroxy, mercapto and nitro.

Another preferred class is that class of compounds wherein $R^1$ is phenyl substituted with one or more halo substituents.

Another preferred group of compounds of formula (Ia) is that group of compounds wherein $R^2$ is —$N(R^5)R^6$; $R^5$ is selected from hydrogen or alkyl; and $R^6$ is selected from hydrogen, alkyl, haloalkyl, carbocyclyl, aryl, aralkyl, heteroalkyl, heterocyclyl, and heterocyclylalkyl.

Of this preferred group of compounds, a preferred subgroup is that subgroup of compounds wherein $R^5$ is selected from hydrogen.

Another preferred subgroup is that subgroup of compounds wherein $R^5$ is hydrogen and $R^6$ is alkyl.

Of the preferred groups, subgroups, classes and subclasses of compounds of formula (Ia) as set forth above, a preferred set of compounds is that set of compounds wherein $R^3$ is selected from —O—$R^7$ or —S(O)$_t$—$R^7$ where t is 0 to 2 and where each $R^7$ is heteroalkyl.

Of this preferred set of compounds, a preferred subset is that subset of compounds wherein the heteroalkyl of $R^7$ has the formula —(CH$_2$)$_n$—C(O)O$R^8$ or —(CH$^2$)$_n$—C(O)N($R^8$)$R^9$ where each n is 1 to 4; each $R^8$ is selected hydrogen, alkyl, aryl, aralkyl, heteroalkyl, heterocyclyl, carbocyclyl and carbocyclylalkyl; and $R^9$ is hydrogen, alkyl or alkoxy.

Of this preferred subset of compounds, preferred compounds are those compounds wherein each $R^8$ is selected from hydrogen and alkyl.

Of the preferred groups, subgroups, classes and subclasses of compounds of formula (Ia) as set forth above, another preferred set of compounds is that set of compounds wherein $R^3$ is selected from —O—$R^7$ or —S(O)$_t$—$R^7$ where t is 0 to 2 and where each $R^7$ is aryl optionally substituted with one or more substituents selected from acyl, alkoxy, alkyl, alkylamino, alkylthio, amino, azido, carboxy, alkoxycarbonyl, aminocarbonyl, alkylaminocarbonyl, cyano, halo, heteroalkyl, hydroxy, mercapto and nitro.

Of this preferred set of compounds, a preferred subset is that subset of compounds wherein the phenyl is optionally substituted with carboxy or alkoxycarbonyl.

Of the preferred groups, subgroups, classes and subclasses of compounds of formula (Ia) as set forth above, another preferred set of compounds is that set of compounds wherein $R^3$ is selected from —O-aralkyl wherein the alkyl group of the aralkyl group is optionally substituted by one or more substituents selected from hydroxy, carboxy or alkoxycarbonyl.

Of the preferred groups, subgroups, classes and subclasses of compounds of formula (Ia) as set forth above, another preferred set of compounds is that set of compounds wherein $R^3$ is —S-alkyl.

Of this preferred set of compounds, a preferred subset of compounds is that subset of compounds wherein $R^3$ is —S—C$_1$–C$_6$alkyl.

Of the preferred compounds of formula (Ia) as set forth above, the preferred compounds are those compounds of formula (Ia) wherein:
$R^1$ is phenyl or benzyl substituted by one or more substituents selected from halo, haloalkyl or haloalkoxy;
$R^2$ is selected from hydrogen and —N($R^5$)$R^6$;
$R^3$ is selected from —O—$R^7$ or —S(O)$_t$—$R^7$ where t is 0 to 2;
$R^4$ is selected from hydrogen, chloro and methyl;
$R^5$ is hydrogen;
$R^6$ is selected from hydrogen, alkyl, haloalkyl, carbocyclyl, aryl, aralkyl, heteroalkyl, heterocyclyl, and heterocyclylalkyl; or
$R^5$ and $R^6$, together with the nitrogen to which they are attached, form morpholinyl, piperidinyl, or pyrrolidinyl; and
$R^7$ is selected from alkyl, aryl, aralkyl, heteroalkyl, heterocyclyl or heterocyclylalkyl.

Of the compounds of formula (Ib) as set forth above in the Summary of the Invention, a preferred group is that group of compounds wherein:
$R^1$ is selected from benzyl and phenyl each substituted by one or more substituents selected from fluoro, trifluoromethyl, and triflouromethoxy;
$R^2$ is selected from hydrogen and —N($R^5$)$R^6$;
$R^3$ is —N($R^{10}$)$R^{11}$;
$R^4$ is selected from hydrogen, halo and alkyl;
$R^5$ is selected from hydrogen and alkyl;
$R^6$ is selected from hydrogen, alkyl haloalkyl, carbocyclyl, aryl, aralkyl, heteroalkyl, heterocyclyl and heterocyclylalkyl; or
$R^5$ and $R^6$, together with the nitrogen to which they are attached, form a heterocyclyl;
$R^{10}$ is selected from hydrogen and alkyl; and
$R^{11}$ is selected from alkyl, aryl, aralkyl, carbocyclyl, carbocyclylalkyl, and heteroalkyl.

Of this group of compounds, a preferred subgroup is that subgroup of compounds wherein:
$R^1$ is selected from 4-fluorophenyl, 4-trifluoromethylphenyl and 4-trifluoromethoxyphenyl;
$R^2$, $R^4$ and $R^{10}$ are each hydrogen; and
$R^{11}$ is selected from carbocyclylalkyl and heteroalkyl.

Of this preferred subgroup of compounds, a preferred class is that class of compounds wherein:
$R^1$ is 4-fluorophenyl;
$R^2$, $R^4$ and $R^{10}$ are each hydrogen; and
$R^{11}$ is carbocyclylalkyl.

Of this preferred class of compounds, a preferred subclass is that subclass of compounds wherein:
$R^1$ is 4-fluorophenyl;
$R^2$, $R^4$ and $R^{10}$ are each hydrogen; and
$R^{11}$ is adamantylmethyl.

Another preferred subgroup of the group of compounds of formula (Ib) as set forth above is that subgroup of compounds wherein:
$R^1$ is 4-fluorophenyl;
$R^2$, $R^4$ and $R^{10}$ are each hydrogen; and
$R^{11}$ is heteroalkyl of the formula —(CH$_2$)$_m$—C(O)O$R^9$ where m is 1 to 4 and $R^9$ is hydrogen or alkyl.

Another preferred group of compounds of formula (Ib) is that group of compounds wherein:
$R^1$ is selected from benzyl and phenyl each substituted by one or more substituents selected from fluoro, trifluoromethyl, and triflouromethoxy;
$R^2$ is selected from hydrogen and —N($R^5$)$R^6$;
$R^3$ is —N($R^{10}$)$R^{11}$;
$R^4$ is selected from hydrogen, halo and alkyl;
$R^5$ is selected from hydrogen and alkyl;
$R^6$ is selected from hydrogen, alkyl, haloalkyl, carbocyclyl, aryl, aralkyl, heteroalkyl, heterocyclyl and heterocyclylalkyl; or
$R^5$ and $R^6$, together with the nitrogen to which they are attached, form a heterocyclyl;
$R^{10}$ and $R^{11}$, together with the nitrogen to which they are attached, form a heterocyclyl.

Of this preferred group of compounds, a preferred subgroup is that subgroup of compounds wherein:
$R^1$ is selected from 4-fluorophenyl, 4-trifluoromethylphenyl and 4-trifluoromethoxyphenyl;
$R^2$ and $R^4$ are each hydrogen; and
$R^{10}$ and $R^{11}$, together with the nitrogen to which they are attached, form piperazinyl.

Of the various groups, subgroups, classes, subclasses, sets and subsets of compounds of the invention as set forth above, the preferred compounds of the invention are selected from the group consisting of the following:

4-[4-(4-bromophenyl)-4-hydroxypiperidin-1-yl]-2-methylsulfanylpyrimidine-5-carboxylic acid (4-fluorophenyl) amide;

[4-[4-(4-bromophenyl)-4-hydroxypiperidin-1-yl]-5-(4-fluorophenylcarbamoyl)pyrimidin-2-yloxy]acetic acid methyl ester;

[4-[4-(4-bromophenyl)-4-hydroxypiperidin-1-yl]-5-(4-fluorophenylcarbamoyl)pyrimidin-2-yloxy]acetic acid benzyl ester;

[4-[4-(4-bromophenyl)-4-hydroxypiperidin-1-yl]-5-(4-fluorophenylcarbamoyl)pyrimidin-2-ylsulfanyl]acetic acid methyl ester;
[4-amino-5-(4-fluorophenylcarbamoyl)pyrimidin-2-ylsulfanyl]acetic acid benzyl ester;
[4-amino-5-(4-fluorophenylcarbamoyl)pyrimidin-2-ylsulfanyl]acetic acid 4-nitro-benzyl ester;
[4-amino-5-(4-fluorophenylcarbamoyl)pyrimidin-2-ylsulfanyl]acetic acid allyl ester;
[4-amino-5-(4-fluorophenylcarbamoyl)pyrimidin-2-ylsulfanyl]acetic acid;
[4-amino-5-(4-fluorophenylcarbamoyl)pyrimidin-2-ylsulfanyl]acetic acid ethyl ester;
[4-amino-5-(4-fluorophenylcarbamoyl)pyrimidin-2-ylsulfanyl]acetic acid methyl ester;
[4-amino-5-(4-fluorophenylcarbamoyl)pyrimidin-2-ylsulfanyl]acetic acid propyl ester;
[4-amino-5-(4-fluorophenylcarbamoyl)pyrimidin-2-ylsulfanyl]acetic acid 4-chloro-benzyl ester;
[4-amino-5-(4-fluorophenylcarbamoyl)pyrimidin-2-ylsulfanyl]acetic acid 2-naphthalen-1-yl-ethyl ester;
[4-amino-5-(4-fluorophenylcarbamoyl)pyrimidin-2-ylsulfanyl]acetic acid biphenyl-4-ylmethyl ester;
[4-amino-5-(4-fluorophenylcarbamoyl)pyrimidin-2-ylsulfanyl]acetic acid 3,5-dimethoxy-benzyl ester;
4-{2-[4-amino-5-(4-fluorophenylcarbamoyl)pyrimidin-2-ylsulfanyl]acetoxymethyl}benzoic acid methyl ester;
[4-amino-5-(4-fluorophenylcarbamoyl)pyrimidin-2-ylsulfanyl]acetic acid pentafluorophenylmethyl ester;
[4-amino-5-(4-fluorophenylcarbamoyl)pyrimidin-2-ylsulfanyl]acetic acid 9H-fluoren-9-yl ester
[4-amino-5-(3,4-difluorobenzylcarbamoyl)pyrimidin-2-ylsulfanyl]acetic acid benzyl ester;
3-[5-(4-fluorophenylcarbamoyl)pyrimidin-2-ylsulfanyl] benzoic acid;
[5-(4-fluorophenylcarbamoyl)pyrimidin-2-yloxy]acetic acid benzyl ester;
[5-(4-fluorophenylcarbamoyl)pyrimidin-2-ylsulfanyl]acetic acid methyl ester;
[5-(4-fluorophenylcarbamoyl)pyrimidin-2-yloxy]acetic acid cyclohexyl ester;
[5-(4-fluorophenylcarbamoyl)pyrimidin-2-yloxy]acetic acid phenyl ester;
[4-amino-5-(4-fluorophenylcarbamoyl)pyrimidin-2-ylsulfanyl]acetic acid 2-phenylethyl ester, and
3-[5-(4-fluorophenylcarbamoyl)pyrimidin-2-ylamino]propionic acid.

Of the methods of using the compounds of the invention as set forth above in the Summary of the Invention, preferred methods are those methods wherein the compounds used therein are the preferred compounds of formula (Ia) and formula (Ib) as set forth above.

Of these preferred methods of using the compounds of the invention, more preferred methods are those methods of treating an inflammatory disorder in a mammal, particularly in a human. Of these more preferred methods, the most preferred methods are those methods of using the compounds of the invention to treat inflammatory disorders which are selected from the group consisting of inflammatory bowel disease, psoriasis, rheumatoid arthritis, acute respiratory distress syndrome, cancer, atherosclerosis, reperfusion injury and graft v. host disease.

Of the pharmaceutical compositions of the invention as set forth above in the Summary of the Invention, the more preferred pharmaceutical compositions are those compositions comprising a pharmaceutically acceptable excipient and a preferred compound of formula (Ia) or formula (Ib) as set forth above.

Preparation of the Compounds of the Invention

It is understood that in the following description, combinations of substituents and/or variables of the depicted formulae are permissible only if such contributions result in stable compounds.

It will also be appreciated by those skilled in the art that in the processes described below the functional groups of intermediate compounds may need to be protected by suitable protecting groups. Such functional groups include hydroxy, amino, mercapto and carboxylic acid. Suitable protecting groups for hydroxy include trialkylsilyl or diaryalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R (where R is alkyl, aryl or aralkyl), p-methoxybenzyl, trityl and the like. Suitable protecting groups for carboxylic acid include alkyl, aryl or aralkyl esters.

Protecting groups may be added or removed in accordance with standard techniques, which are well-known to those skilled in the art and as described herein.

The use of protecting groups is described in detail in Green, T. W. and P. G. M. Wutz, Protective Groups in Organic Synthesis (1991), 2nd Ed., Wiley-Interscience. The protecting group may also be a polymer resin such as a Wang resin or a 2-chlorotrityl chloride resin.

It will also be appreciated by those skilled in the art, although such protected derivatives of compounds of formula (I) as described above in the Summary of the Invention, may not possess pharmacological activity as such, they may be administered to a mammal having an inflammatory or autoimmune disorder, or a pulmonary and respiratory tract inflammation, and thereafter metabolized in the body to form compounds of the invention which are pharmacologically active. Such derivatives may therefore be described as "prodrugs". All prodrugs of compounds of formula (I) are included within the scope of the invention.

It is understood that one of ordinary skill in the art would be able to make the all the compounds of the invention in light of the following disclosure, including the Examples, and information known to those of ordinary skill in the chemical synthesis field.

Compounds of the present invention may be prepared from readily available starting materials according to methods set forth in the synthetic schemes below. For example, compounds of formula (Ia) can be prepared as illustrated below in Scheme 1.

SCHEME 1

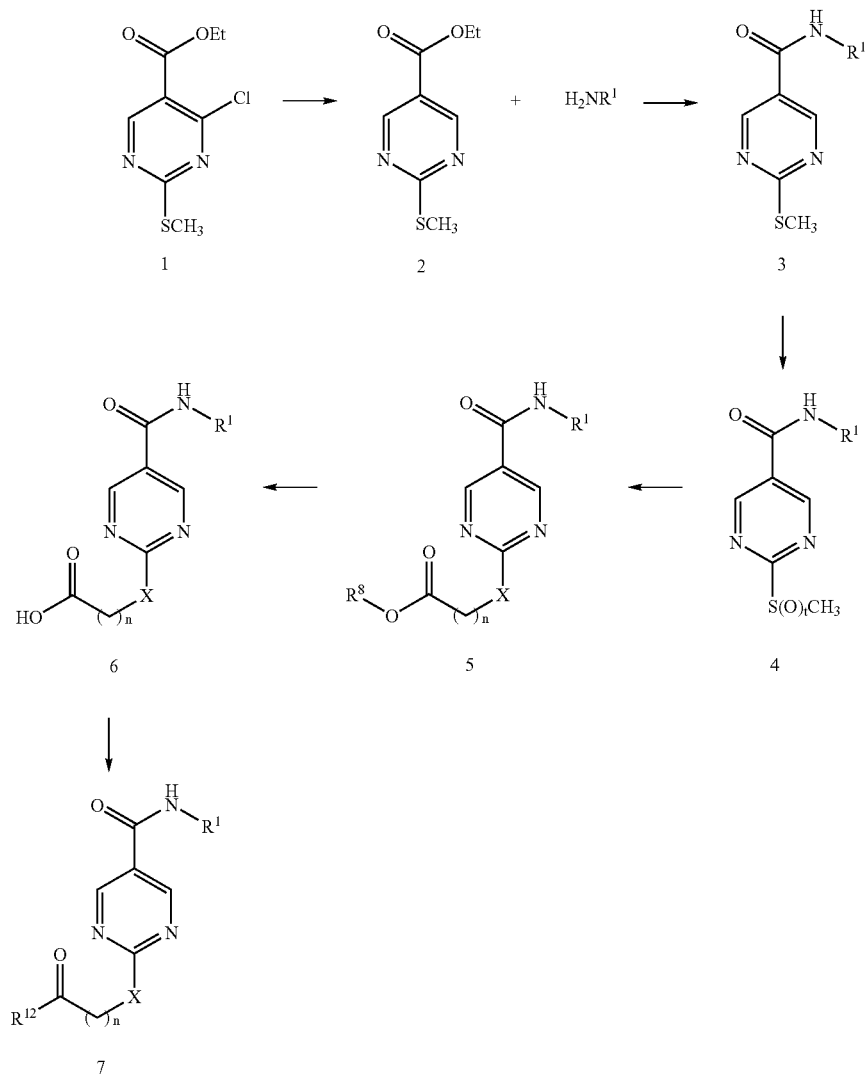

As illustrated above, ethyl 4-chloro-2-thiomethylpyrimidine-4-carboxylate, Compound 1, can be reduced to afford the corresponding deschloropyrimidine, Compound 2. Suitable reduction conditions are known in the art, and include treatment of Compound 1 with a palladium catalyst in the presence of magnesium oxide in an alcoholic solvent, e.g., ethanol.

Exposure of Compound 2 to an anilide compound can be used to provide the corresponding Compound 3. Anilide compounds are readily prepared by deprotonation of the corresponding aniline compound of the formula $H_2N—R^1$, wherein $R^1$ is as defined above in the Summary of the Invention, by treatment of the aniline compound with base, e.g., potassium tert-butoxide. If the $R^1$ group of the aniline contains a base-sensitive substituent, then that substituent may be protected using a protecting group according to methods known in the art. The deprotonation reaction is typically run in a suitable solvent, e.g., THF. The sulfur atom of Compound 3 can then be oxidized to the corresponding sulfone or sulfoxide or sulfone-sulfoxide mixture (Compound 4 where t is 1 or 2) through treatment with an oxidizing agent such as meta-chloroperbenzoic acid, peracetic acid or oxone, in a solvent such as DMF, DCM or DCM/THF mixtures.

Compound 4 is itself a compound of the present invention. In addition, Compound 4 can be used as the pure sulfoxide, pure sulfone, or a mixture of sulfoxide and sulfone in order to provide additional compounds of the present invention. For instance, Compound 4 can undergo a substitution reaction with a variety of oxygen and sulfur nucleophiles in order to provide a variety of $R^3$ groups to compounds of the present invention. For instance, Compound 4 may undergo a displacement reaction with reagents of the formula $HX—CH_2—(CH_2)_m—C(O)OR^8$ wherein X is oxygen or sulfur, m is zero or an integer from 1 to about 10, and $R^8$ is alkyl, aryl, aralkyl, heteroalkyl, heterocyclyl, carbocyclyl and carbocyclylalkyl to thereby provide Compound 5. These displacement reactions can be performed in THF, DMF, NMP or other appropriate solvent(s), and are typically performed under basic conditions using a base such as potassium tert-butoxide, diisopropylethylamine (DIPEA), sodium hydride, or diazobicyclundecane (DBU). The displacement reaction can also be done using the free thiol or free alcohol as both reactive reagent and solvent under basic conditions. The displacement reaction is typically performed at ambient temperature, and is essentially complete after a reaction time of from about 15 minutes to 24 hours.

Exposure of Compound 5 to saponification conditions, e.g., treatment of Compound 5 with aqueous sodium hydroxide, results in saponification of the ester functional group and affords the corresponding carboxylic acid, Compound 6. Compound 6 can be isolated and subsequently used in a coupling reaction to afford the corresponding Compound 7 where $R^{12}$ is —$OR^8$ or —$N(R^8)R^9$ where each $R^8$ is alkyl, aryl, aralkyl, heteroalkyl, heterocyclyl, carbocyclyl and carbocyclylalkyl and $R^9$ is hydrogen, alkyl or alkoxy. For instance, coupling of Compound 6 with alcohols of the formula $R^{12}$—OH can be used to form Compound 7 where $R^{12}$ is —$OR^8$. This coupling reaction may be accomplished using coupling agents such as TSTU, DCC, or EDC in the presence of base such as DIPEA or DMAP. Similarly, amide bonds can be constructed by coupling Compound 6 with an amine of the formula $HN(R^8)R^9$ to form Compound 7 wherein $R^{12}$ is —$N(R^8)R^9$. The amide-forming coupling reaction can be accomplished using EDC or other suitable coupling reagents to give Compound 7.

An alternative method for constructing amides of the invention involves the pre-activation of Compound 6 through attachment to a 4-hydroxyphenylsulfonyl polystyrene resin using DIC as a coupling agent. The resulting resin-bound intermediate can be treated with various amine nucleophiles in DMF, or using the amines as solvent, to produce Compound 7 where $R^{12}$ is —$N(R^8)R^9$. These amide bond-forming reactions are typically performed at 50° C. for several days.

Another method of preparing the compounds of formula (Ia) is illustrated below in Scheme 2:

SCHEME 2

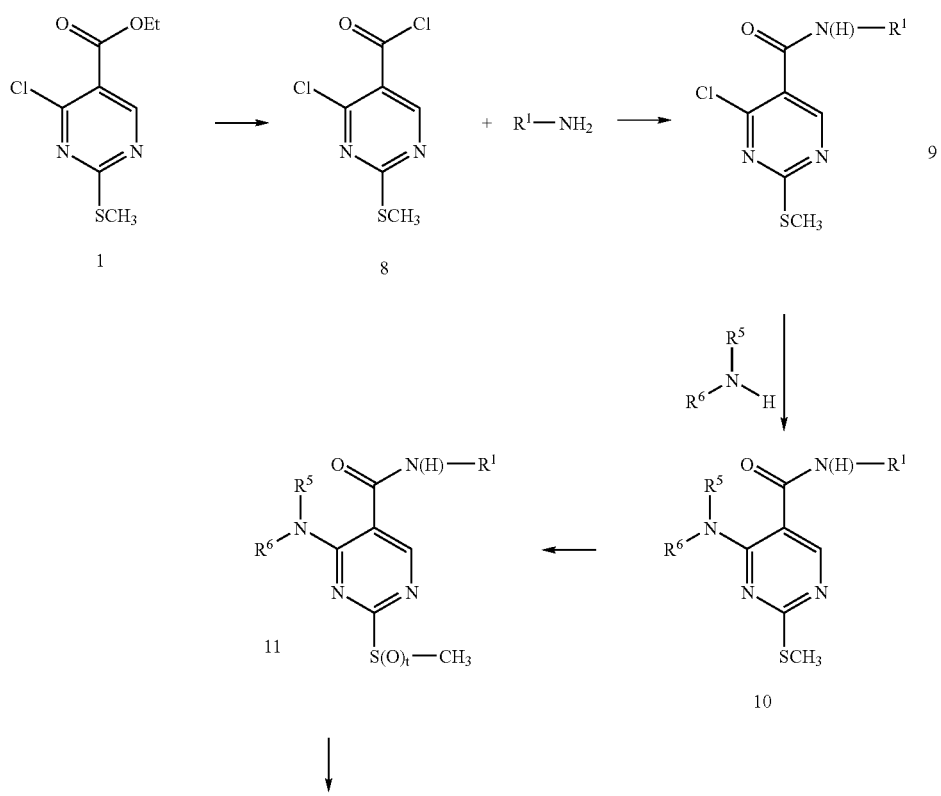

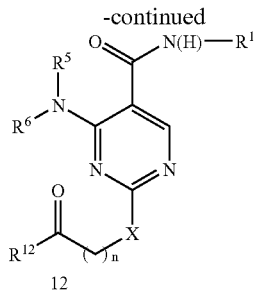

12

As illustrated above, Compound 1 (which is the starting material for Scheme 1) may be converted to the corresponding acid chloride in a two-step procedure. For example, Compound 1 may be treated with potassium trimethylsilyloxide in 1,2-dimethoxyethane followed by treatment with thionyl chloride in the presence of a catalytic quantity of DMF to afford Compound 8. Exposure of Compound 8 to primary amines of the formula $R^1$—$NH_2$ in the presence of a base such as DIPEA affords Compound 9. Suitable solvents for this amide bond formation include THF, and DCM. Compound 9 can be further reacted with aqueous ammonia, a primary amine of the formula $H_2N(R^5)$ or a secondary amine of the formula $HN(R^5)R^6$ to afford Compound 10. This chloride displacement reaction can be achieved in a number of solvents including DMF, DCM and THF, and is typically performed in the presence of excess amine or with a stoichiometric amount of amine reactant and a base such as DIPEA. The reaction can typically proceed at 20° C. to 100° C. in 5 minutes to 48 hours.

The sulfur atom of Compound 10 can be oxidized to the corresponding sulfone, sulfoxide or sulfone-sulfoxide mixture, Compound 11 (where t is 1 or 2), through treatment of Compound 10 with an oxidizing agent such as meta-chloroperbenzoic acid (MCPBA), peracetic acid, or oxone, in a solvent such as DMF, DCM or DCM/THF mixtures. Compound 11, used as pure sulfoxide, pure sulfone, or a mixture of sulfoxide and sulfone, may undergo substitution reactions with a variety of oxygen and sulfur nucleophiles. These include a displacement reaction with reagents of the formula HX—$CH_2$—$(CH_2)_m$—$C(O)OR^8$ wherein X is oxygen or sulfur, m is zero or an integer from 1 to about 10, and $R^8$ is alkyl, aryl, aralkyl, heteroalkyl, heterocyclyl, carbocyclyl and carbocyclylalkyl to provide Compound 12 where n is an integer from 1 to about 10 and $R^{12}$ is —$OR^8$. These displacement reactions can be performed in THF, DMF, NMP or other appropriate solvents, and are typically done under basic conditions using potassium tert-butoxide, diisopropylethylamine (DIPEA), sodium hydride, diazobicyclundecane (DBU) or other suitable bases. The displacement reactions can also be done using the free thiol or free alcohol as both reactive reagent and solvent under basic condition. These reactions are typically performed at ambient temperature from over 15 min to 24 hours. Treatment of Compound 12 when $R^{12}$ is —$OR^8$ where $R^8$ is alkyl with aqueous sodium hydroxide results in saponification of the ester functional group to afford Compound 12 where $R^{12}$ is hydroxy, which can be further treated as described above for Compounds 6 in Scheme 1 to form Compound 12 where $R^{12}$ is —$OR^8$ or —$N(R^8)R^9$ where each $R^8$ can be alkyl, aryl, aralkyl, heteroalkyl, heterocyclyl, carbocyclyl or carbocyclylalkyl and $R^9$ is hydrogen, alkyl or alkoxy.

Another alternative approach for preparing compounds of the present invention is illustrated below in Scheme 3:

SCHEME 3

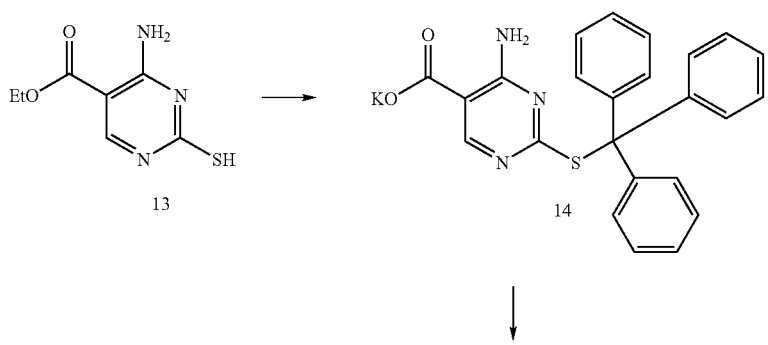

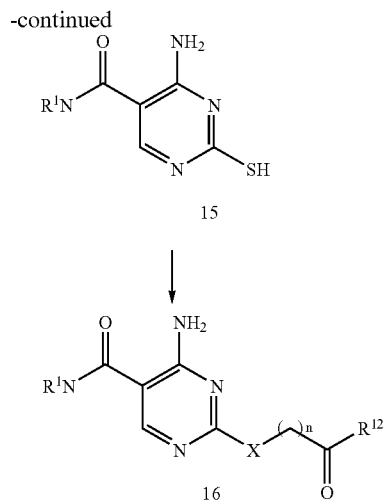

As illustrated above, 4-amino-2-mercaptopyrimidine-5-carboxylic acid ethyl ester, Compound 13, which is commercially available from Lancaster Synthesis, is S-tritylated with triphenylmethyl chloride in DMSO using sodium carbonate as base, and the compound was converted to the potassium carboxylate salt, Compound 14, using potassium trimethylsilyloxide. Compound 14 could be used in amide bond forming reactions using the coupling reagent HATU in NMN with the base NMM and the trityl protecting group could be removed using acetic acid in ether to afford Compound 15. Compound 15 could then be treated with the appropriate alcohol or thiol as described above in Scheme 1 and Scheme 2 to provide the Compound 16 where $R^{12}$ is —$OR^8$ or —$N(R^8)R^9$ where each $R^8$ is alkyl, aryl, aralkyl, heteroalkyl, heterocyclyl, carbocyclyl and carbocyclylalkyl and $R^9$ is hydrogen, alkyl or alkoxy. In the case where $R^{12}$ is an alkoxy group, Compound 16 can be hydrolyzed in aqueous base or with potassium trimethylsilyloxide to produce the analogous acids.

Compounds of formula (Ib) as described above in the Summary of the Invention may be prepared by reacting Compounds 3, 4, 9, 10, 11, or 15, as described above, with the appropriate amine under conditions described in the following Examples.

All compounds of the invention as prepared above which exist in free base or acid form may be converted to their pharmaceutically acceptable salts by treatment with the appropriate inorganic or organic base or acid. Salts of the compounds prepared above may be converted to their free base or acid form by standard techniques. It is understood that all polymorphs, amorphous forms, anhydrates, hydrates, solvates and salts of the compounds of the invention are intended to be within the scope of the invention.

The following specific Examples are provided as a guide to assist in the practice of the invention, and are not intended as a limitation on the scope of the invention.

EXAMPLE 1

Synthesis of 2-(2-Hydroxyethylsulfanyl)pyrimidine-5-carboxylic acid (4-fluorophenyl)amide and 2-(2-Hydroxyethylsulfinyl)pyrimidine-5-carboxylic Acid (4-fluorophenyl)amide and other compounds of formula (Ia) and (Ib)

While the following preparation uses 4-fluoroaniline as a starting material, it will be apparent to one of ordinary skill in the art that many other substituted aniline compounds could be used in lieu of 4-fluoroaniline. Other substituted aniline compounds are commercially available chemicals, or are compounds described in the chemical literature. If the substituted aniline compound contains a base-sensitive group, then that group may be protected with a suitable protecting group according to techniques known in the art (see, e.g., Greene and Wuts, Protective Groups in Organic Synthesis, 2d Edition, John Wiley & Sons, New York, 1991). In this manner, the present invention provides a very large number of pyrimidine carboxylates having aryl as the $R^1$ group.

A. 2-Methylsulfanylpyrimidine-5-carboxylic acid ethyl ester

To a round bottom flask containing a slurry of ethyl-4-chloro-2-thiomethylpyrimidine-4-carboxylate (2.32 g, 10 mmol) in ethanol (15 mL), water (6 mL) and THF (6 mL) was added MgO (403 mg, 10 mmol) and 10% Pd/C (2.3 g, 2.2 mmol Pd). The flask was evacuated, purged with $H_2$ and the contents allowed to react under 1 atm $H_2$ for 3 h. The system was again evacuated and purged with $N_2$. After dilution with ethyl acetate, Celite and $Na_2SO_4$ were added, and the solution filtered through a pad of Celite. The filter cake was washed with ethyl acetate and the combined filtrates concentrated in vacuo to afford a colorless oil. A 10% ethyl acetate/hexane solution of the crude product was passed through a plug of $SiO_2$ to afford 1.635 g (83% yield) of the titled product.

B. 2-Methylsulfanylpyrimidine-5-carboxylic acid (4-fluorophenyl)amide

To a solution of potassium tert-butoxide (1 M in THF, 66 mL, 66 mmol) in THF (66 mL) in an ice bath was added 4-fluoroaniline over 1.5 min. The solution was stirred for 1 min, then a solution of 2-methylsulfanyl-pyrimidine-5-carboxylic acid ethyl ester (3.745 g, 18.9 mmol) in THF (30 mL) was added via syringe over 4 min. The syringe was washed with 4 mL THF, and the reaction allowed to proceed for 5 min. The reaction was quenched with 1% HCl (450 mL) resulting in a solid precipitate. The solution was filtered, and the solids washed with water. After drying, the solids were triturated with 10% ethyl acetate/hexane to afford 4.0 g (80% yield) of the titled product as a pale yellow solid, which was used in the following preparations.

C. 2-[(Adamantan-1-ylmethyl)amino]pyrimidine-5-carboxylic acid (4-fluorophenyl)amide To a solution of 2-methylsulfanylpyrimidine-5-carboxylic acid (4-fluorophenyl)amide (50 mg, 0.19 mmol) in 4/1 dioxane/water (0.6 mL) in a sealed tube was added 1-adamantanemethyl amine (250 µL, 1.4 mmol). The solution was heated at 110° C. for 18 h, cooled, diluted with 3% HCl and then poured into water to form a precipitate. The solids were collected by filtration, washed with water and dried. Trituration of the solids with ethyl acetate at about 70° C., followed by a hot filtration and washing with hexane, afforded 16.7 mg (24% yield) of the titled product as a white solid. API-MS m/z 381 (MH)$^+$, 379 (M–H)$^-$.

D. 2-{4-[(Methylphenylcarbamoyl)methyl]piperazin-1-yl}pyrimidine-5-carboxylic acid (4-fluorophenyl)amide The titled compound was synthesized in a manner analogous to 2-[(adamantan-1-ylmethyl)amino]pyrimidine-5-carboxylic acid (4-fluorophenyl)amide, with the exception that the hot trituration was omitted. Yield of the title compound was 48%. API-MS m/z 449 (MH)$^+$, 447 (M–H)$^-$.

E. 2-Methanesulfinylpyrimidine-5-carboxylic acid (4-fluorophenyl)amide

To a solution of 2-methylsulfanylpyrimidine-5-carboxylic acid (4-fluorophenyl)amide (2.00 g, 7.60 mmol) in dichloromethane (76 mL) was added m-CPBA (67%, 2.02 g, 7.84 mmol) in one portion. Solid precipitate appeared within 2 min, and after 10 min the solution was diluted with 2/1 dichloromethane/hexane (60 mL). The solids were collected by filtration and washed with 50% dichloromethane/hexane to afford, after drying, 1.558 g (73% yield) of the titled sulfoxide. A second crop was obtained by concentrating the filtrate and triturating the solids first with hot 2/1 dichloromethane/hexane, and then after filtration by a second trituration with acetone. An additional 0.22 g (10%) of titled product was obtained, and was shown by $^1$H NMR to be contaminated with 10% sulfone.

F. The compound prepared above in Paragraph E, i.e., 2-methanesulfinylpyrimidine-5-carboxylic acid (4-fluorophenyl)amide, is a convenient precursor to a wide number of compounds of the present invention, including the following compounds. As illustrated in the many examples set forth below, the sulfoxide compound may be reacted with any of a large number of thiol compounds (i.e., compounds having a —SH group) or hydroxy compounds (i.e., compounds having a —OH group) so as to provide pyrimidine carboxamide compounds wherein R$^3$ is selected from —O—R$^7$ or —S(O)$_t$—R$^7$ where R$^7$ is as defined above in the Summary of the Invention. Suitable thiol and hydroxy compounds are commercially available chemicals, or are compounds described in the chemical literature. If the thiol or hydroxy compound contains a functional group that is incompatible with the reaction conditions, then that group may be protected with a suitable protecting group according to techniques known in the art (see, e.g., Greene and Wuts, Protective Groups in Organic Synthesis, 2d Edition, John Wiley & Sons, New York, 1991). As stated previously, the sulfoxide compound may be prepared with anilines other than 4-fluoroaniline, so as to provide a very wide range of pyrimidine carboxamides having various R$^1$ and R$^3$ groups.

1. 2-(2-Hydroxyethylsulfanyl)pyrimidine-5-carboxylic acid (4-fluorophenyl)amide To a solution of 2-methanesulfinylpyrimidine-5-carboxylic acid (4-fluorophenyl)amide (39 mg, 0.14 mmol) in THF (1 mL) was added β-mercaptoethanol (20 µL, 0.28 mmol) followed by DBU (43 µL, 0.28 mmol). After 15 min the reaction was quenched with 40 mL 1% HCl, resulting in the formation of solids. The solids were collected by filtration and washed with water. The filtrate was extracted with dichloromethane to afford a white solid after concentration. These were combined with the solids isolated from the filtration and passed through a plug of SiO$_2$ using 60% ethyl acetate/hexane to afford a white solid. After trituration with dichloromethane/hexane, 19.3 mg (47% yield) of titled product was obtained. API-MS m/z 294 (MH$^+$), 292 (M–H)$^-$.

2. 3-[5-(4-Fluorophenylcarbamoyl)pyrimidin-2-ylsulfanyl]benzoic acid

To a solution of 3-mercaptobenzoic acid (83 mg, 0.54 mmol) in THF (2.5 mL) was added potassium tert-butoxide (1 M in THF, 1.1 ML, 1.1 mmol). After 3 min, 2-methanesulfinylpyrimidine-5-carboxylic acid (4-fluorophenyl)amide was added in one portion and the solution was stirred for 24 h. Water was added, and then the solution was poured into 3% HCl to precipitate the product. The solids were collected by filtration and washed with water. Flash chromatography on SiO$_2$ using a gradient of 5% methanol/dichloromethane to 10% methanol/dichloromethane afforded 15.1 mg (23% yield) of the titled thioether as a white solid. API-MS m/z 370 (MH$^+$), 368 (M–H)$^-$.

3. 3-[5-(4-Fluorophenylcarbamoyl)pyrimidin-2-ylsulfanyl]propionic acid

To a solution of solution of 2-methanesulfinylpyrimidine-5-carboxylic acid (4-fluorophenyl)amide (141 mg, 0.50 mmol) in THF (3 mL) was added 3-mercaptopropionic acid (88 µL, 1.0 mmol) followed by DBU (320 µL, 2.1 mmol). The solution was stirred for 25 min, diluted with 1% NaHCO$_3$, and extracted with ethyl acetate. The aqueous layer was acidified with 3% HCl to afford a white precipitate. The solids were collected by filtration, washed with water and dried to afford 128.8 mg (79% yield) of the titled compound as a white solid. API-MS m/z 322 (MH$^+$), 320 (M–H)$^-$.

4. 3-[5-(4-Fluorophenylcarbamoyl)pyrimidin-2-ylsulfanyl]propionic acid methyl ester To a solution of 2-methanesulfinylpyrimidine-5-carboxylic acid (4-fluorophenyl)amide (50 mg, 0.18 mmol) in THF (0.9 mL) was added methyl-3-mercaptopropionate (40 µL, 0.36 mmol) followed by DBU (60 µL, 0.40 mmol). The solution was stirred for 1 h, diluted with 25% ethyl acetate/hexane and passed through a plug of SiO$_2$ washing with 50% ethyl acetate/hexane. The filtrate was concentrated, and the resulting solids triturated with 20% ethyl acetate/hexane to

5. (S)-2-[5-(4-Fluorophenylcarbamoyl)pyrimidin-2-yloxy]propionic acid methyl ester To a solution of 2-methanesulfinylpyrimidine-5-carboxylic acid (4-fluorophenyl)amide (40 mg, 0.14 mmol) in THF (1 mL) was added (R)-(+)-methyl lactate (20 µL, 0.21 mmol) followed by DBU (34 µL, 0.23 mmol). The solution was stirred for 2 days, quenched with 3% HCl and extracted with ethyl acetate. The organic layers were combined, washed successively with 5% $NaHCO_3$, water, and brine, dried and concentrated in vacuo to afford 19.9 mg (46% yield) of the titled compound as a white solid shown to be 94% pure by HPLC. ESI-MS m/z 320 (MH$^+$), 318 (M–H)$^-$.

6. [5-(4-Fluorophenylcarbamoyl)pyrimidin-2-yloxy]acetic acid benzyl ester

To a solution of 2-methanesulfinylpyrimidine-5-carboxylic acid (4-fluorophenyl)amide (173 mg, contaminated with 10% sulfone, 0.62 mmol) in THF (6 mL) was added benzyl glycolate (128 µL, 0.90 mmol) followed by potassium tert-butoxide (1 M in THF, 0.3 mL, 0.3 mmol) and DBU (139 µL, 0.93 mmol). The solution was stirred for 5 h, diluted with 50% ethyl acetate/hexane, and passed through a plug of $SiO_2$ followed by washing with 40% ethyl acetate/hexane. The filtrate was concentrated in vacuo, and the residue flash-chromatographed on $SiO_2$ with 35% ethyl acetate/hexane to afford 71.5 mg (30% yield) of the titled product as a white solid. ESI-MS m/z 382 (MH$^+$), 380 (M–H)$^-$.

7. (R)-[5-(4-Fluorophenylcarbamoyl)pyrimidin-2-yloxy]phenylacetic acid methyl ester A suspension of 2-methanesulfinylpyrimidine-5-carboxylic acid (4-fluorophenyl)amide (100 mg, 0.36 mmol) and (R)-(−)-methyl mandelate (86 mg, 0.52 mmol) in 3.6 mL of THF was treated dropwise with DBU (80 µL, 0.54 mmol) at ambient temperature. The reaction mixture clarified and turned yellow over the course of 5 min. The reaction was quenched after 24 hours by the addition of 5 mL of 1 M HCl. The mixture was extracted with 2×25 mL portions of ethyl acetate. The organic extracts were combined, dried using $Na_2SO_4$ and concentrated in vacuo. The crude material was dissolved in 30% (v/v) ethyl acetate/hexanes and filtered though a 10 g plug of silica gel. The eluent was concentrated to dryness and triturated with 3×5 mL portions of hexane followed by 3×10 mL portions of 10% (v/v) portions of ethyl acetate/hexanes. The residue was dried to yield 47 mg (34%) of the titled compound as a white solid. ESI-MS m/z 382 (MH$^+$), 380 (M–H)$^-$.

8. (S)-[5-(4-Fluorophenylcarbamoyl)pyrimidin-2-yloxy]phenylacetic acid methyl ester A suspension of 2-methanesulfinylpyrimidine-5-carboxylic acid (4-fluorophenyl)amide (100 mg, 0.36 mmol) and (S)-(+)-methyl mandelate (86 mg, 0.52 mmol) in 3.6 mL of THF was treated dropwise with DBU (80 µL, 0.54 mmol) at room temperature. The reaction mixture clarified and turned yellow over the course of 5 min. The reaction was quenched after 24 hours by the addition of 5 mL 1 M HCl, followed by 25 mL of 1:1 (v:v) ethyl acetate:water. The mixture was extracted with 2×25 mL portions of ethyl acetate. The organic extracts were combined, dried using $Na_2SO_4$ and concentrated in vacuo. The crude material was dissolved in 30% (v/v)-ethyl acetate/hexanes and chromatographed through 15 g silica gel, followed by a second chromatography through 20 g silica gel. The product fractions were concentrated to yield 15 mg (11%) of the titled compound as a white solid. ESI-MS z/z 382 (MH$^+$), 380 (M–H$^-$).

9. [5-(4-Fluorophenylcarbamoyl)pyrimidin-2-yloxy]acetic acid ethyl ester

Reaction conditions and work-up were essentially as described above, but (R)-(+)-methyl lactate (50 µL, 0.52 mmol) was used as the reactant. Crude product was chromatographed through 15 g silica gel (5% methanol/dichloromethane+0.5% acetic acid). The product fractions were concentrated to afford 53 mg (46% yield) of the titled compound. ESI-MS m/z 320 (MH$^+$), 318 (M–H$^-$).

10. [5-(4-Fluorophenylcarbamoyl)pyrimidin-2-yloxy]acetic acid ethyl ester

Reaction conditions were essentially as described above, but using ethyl glycolate (49 µL, 0.52 mmol) used as the reactant. The reaction was quenched with 20 mL of 0.05 M $HCl_{(aq)}$ and filtered. The product cake was rinsed with 2×10 mL portions of water. The mixed white and yellow solids afforded 34 mg (30% yield) of the titled compound.

11. 2-[5-(4-Chlorophenyl)-2-methylfuran-3-ylmethoxy]-pyrimidine-5-carboxylic acid (4-fluorophenyl)amide To a solution of 2-methanesulfinylpyrimidine-5-carboxylic acid (4-fluorophenyl)amide (60 mg, 0.215 mmol) in THF (1 mL) was added [2-(4-chlorophenyl)-5-methylfuran-3-yl]methanol (96 mg, 0.43 mmol) followed by DBU (65 µL, 0.43 mmol). The reaction was stirred for 1 h, diluted with 50% dichloromethane/hexane, and passed through a plug of $SiO_2$ washing with 30% ethyl acetate/hexane. The filtrate was concentrated in vacuo, and the resulting solids were triturated with 20% ethyl acetate/hexane to afford 44.5 mg (47% yield) of the titled product as a white solid. ESI-MS m/z 438 (MH$^+$) and 440 (M+2)H$^+$, 436 (M–H)$^-$ and 438 ((M+2)–H)$^-$.

12. 3-[5-(4-Fluorophenylcarbamoyl)pyrimidin-2-ylamino]-propionic acid tert-butyl ester To a solution of 2-methanesulfinylpyrimidine-5-carboxylic acid (4-fluorophenyl)amide (76.2 mg, 0.27 mmol) in THF (2 mL) was added 0-alanine tert-butyl ester hydrochloride (245 mg, 1.35 mmol) followed by diisopropylethyl amine (235 µL, 1.35 mmol). The solution was stirred for 30 min, and then poured into 1% HCl (40 mL), resulting in the formation of a solid precipitate. The solids were collected by filtration, washed with water and dried to afford 86.4 mg (88% yield) of the titled product as a white solid. API-MS m/z 305 (M–56)H$^+$, 359 (M–H)$^-$.

13. 3-[5-(4-Fluorophenylcarbamoyl)pyrimidin-2-ylamino]-propionic acid

A solution of 3-[5-(4-fluorophenylcarbamoyl)pyrimidin-2-ylamino]propionic acid tert-butyl ester in 90% trifluoroacetic acid/water was stirred for 15 min. Toluene (4 mL) was added and the solution was concentrated in vacuo. A series of dilutions and concentrations were performed using acetic acid/toluene (1/1) followed by methanol/toluene (1/1). The resulting solids were triturated with ethyl acetate/hexane (2/1) to afford 61.1 mg (98% yield) of the titled product as a white solid. API-MS m/z 305 (MH)$^+$, 303 (M–H)$^-$.

EXAMPLE 2

Synthesis of [5-(4-Fluorophenylcarbamoyl)pyrimidin-2-ylsulfanyl]acetic acid methyl ester and Hydrolysis Product Thereof and Esterification Product Thereof A. [5-(4-Fluorophenylcarbamoyl)pyrimidin-2-ylsulfanyl]acetic acid methyl ester To a solution of 2-methanesulfinylpyrimidine-5-carboxylic acid (4-fluorophenyl)amide (prepared as in Example 1, 109.5 mg, 0.39 mmol) in THF (2 mL) was added methyl-2-mercaptoacetate (75 µL, 0.79 mmol) followed by DBU (120 µL, 0.81 mmol). After 5 min the reaction mass was poured into 1% HCl, resulting in the formation of a solid precipitate. The solids were collected by filtration, washed with water and dried to afford 112.5 mg (89% yield) of the titled methyl ester as a white solid. API-MS m/z 322 (MH$^+$), 320 (M–H)$^-$.

B. [5-(4-Fluorophenylcarbamoyl)pyrimidin-2-ylsulfanyl]acetic acid

To a solution of [5-(4-fluorophenylcarbamoyl)pyrimidin-2-ylsulfanyl]acetic acid methyl ester (95.5 mg, 0.3 mmol) in THF (2 mL) and methanol (0.25 mL) was added 1 N NaOH (0.3 mL). After 20 min an additional 0.2 mL of 1 N NaOH was added, and after 40 min an additional 0.1 mL 1 N NaOH was added. After 45 min total reaction time the solution was diluted with water and extracted with ethyl acetate. The organic layers were combined and washed once with water. The aqueous layers were combined and acidified to pH 1 with 3% HCl resulting in the formation of a solid precipitate. The solids were collected by filtration, washed and dried to afford 79.9 mg (88% yield) of the titled acid as a pale beige solid. API-MS m/z 308 (MH$^+$), 306 (M–H)$^-$.

C. [5-(4-Fluorophenylcarbamoyl)pyrimidin-2-ylsulfanyl]acetic acid 3-fluoro-benzyl ester To a solution of [5-(4-fluorophenylcarbamoyl)pyrimidin-2-ylsulfanyl]acetic acid (40 mg, 0.13 mmol) in THF (1 mL) was added diisopropylethylamine (45 µL, 0.26 mmol) and TSTU (55 mg, 0.18 mmol). After stirring for 5 min, 3-fluorobenzyl alcohol (18 µL, 0.17 mmol) and DMAP (18 mg, 0.15 mmol) were added and the solution was stirred for 18 h. Ethyl acetate was added, and the reaction was quenched with 3% HCl. The layers were separated, and the organic layer was washed successively with 5% NaHCO$_3$, water, and brine. The brown organic layer was passed through a plug of SiO$_2$ and washed with 50% ethyl acetate/hexane. The filtrate was concentrated to afford a yellow solid. Flash chromatography through SiO$_2$ using 25% ethyl acetate/hexane afforded 15.0 mg (28% yield) of the titled product as a white solid. ESI-MS m/z 416 (MH$^+$), 414 (M–H)$^-$.

D. The foregoing synthetic transformations illustrate the formation of a carboxylic acid ester, the hydrolysis of that ester to form a carboxylic acid, and the esterification of that carboxylic acid with a different alcohol. As will be appreciated by one of ordinary skill in the art, the carboxylic acid is a convenient precursor to a wide number of compounds of the present invention. The carboxylic acid may be reacted with any of a large number of alcohol compounds (i.e., compounds of the formula HO—R) so as to provide pyrimidine carboxamide compounds wherein R$^3$ is selected from R—OC(=O)—R'—S—. Suitable alcohol compounds are commercially available chemicals, or are compounds described in the chemical literature. If the alcohol compound contains a functional group that is incompatible with the reaction conditions, then that group may be protected with a suitable protecting group according to techniques known in the art (see, e.g., Greene and Wuts, Protective Groups in Organic Synthesis, 2d Edition, John Wiley & Sons, New York, 1991).

EXAMPLE 3

Synthesis of [5-(4-Fluorophenylcarbamoyl)Pyrimidin-2-yloxy]-Acetic Acid Methyl Ester and Hydrolysis Product Thereof A. [5-(4-Fluorophenylcarbamoyl)pyrimidin-2-yloxy] acetic acid methyl ester To a solution of 2-methanesulfinylpyrimidine-5-carboxylic acid (4-fluorophenyl)amide (prepared as in Example 1, 150 mg, 0.535 mmol) in THF (2 mL) was added methyl glycolate (82.5 µL, 1.07 mmol) followed by DBU (160 µL, 1.07 mmol). The reaction was stirred for 5 h, diluted with 3/6/1 ethyl acetate/hexane/dichloromethane, and passed through a plug of SiO$_2$ using 4/5/1 ethyl acetate/hexane/dichloromethane. The filtrate was concentrated, and the resulting solids triturated with dichloromethane/hexane to afford 95.1 mg (58% yield) of the titled ester as a white solid. ESI-MS m/z 306 (MH$^+$), 304 (M–H)$^-$.

B. [5-(4-Fluorophenylcarbamoyl)pyrimidin-2-yloxy] acetic acid

To a solution of [5-(4-fluorophenylcarbamoyl)pyrimidin-2-yloxy]acetic acid methyl ester (prepared above, 82 mg, 0.269 mmol) in THF/methanol (6 mL/0.3 mL) was added 1 N NaOH (0.3 mL, 0.3 mmol). Additional 1 N NaOH aliquots were added after 5 min (0.15 mL), 25 min (0.25 mL), and 2 h (1.0 mL). By thin layer chromatography (15/84/1 methanol/dichloromethane/acetic acid) it appeared that the starting material never disappeared, but LC/MS showed the presence of mostly methyl ether, with some desired acid and no starting material. The reaction mass was extracted with ethyl acetate. The combined organic layers were washed 1× with water, then 2× with 5% NaHCO$_3$. The aqueous layers were combined, acidified to pH 1 with 3% HCl and extracted with dichloromethane. The organic layers were combined, washed with brine, dried and concentrated in vacuo to afford 12.8 mg (16% yield) of the titled carboxylic acid as a white solid. ESI-MS m/z 292 (MH$^+$), 290 (M–H)$^-$.

As illustrated below, this carboxylic acid compound may be esterified with a large number of alcohols, so as to produce the corresponding carboxylic acid ester.

C. [5-(4-Fluorophenylcarbamoyl)pyrimidin-2-yloxy] acetic acid cyclohexyl ester

A mixture of [5-(4-fluorophenylcarbamoyl)pyrimidin-2-yloxy]acetic acid methyl ester (prepared above, 50 mg, 0.17 mmol) and cyclohexanol (51 mg, 0.51 mmol) were slurried in dichloromethane. DMAP (17 mg, 0.14 mmol) was added, and the slurry became homogeneous and colorless. The solution was then treated with 1 M dicyclohexylcarbodiimide (190 µL, 0.19 mmol), which initiated formation of a white slurry within 5 min. After 1 h, thin layer chromatography indicated complete conversion. The reaction was quenched with 10 mL 1 M $HCl_{(aq)}$ and 25 mL dichloromethane. The phases were partitioned, and the aqueous phase extracted with 5 mL dichloromethane. The organic phases were combined and sequentially washed with 10 mL portions of 0.1 M $HCl_{(aq)}$, saturated. $NaHCO_{3(aq)}$ and brine. The organic layer was dried using $Na_2SO_4$, filtered and concentrated. The 101 mg of crude product was chromatographed over $SiO_2$ (1:1 ethyl acetate:hexane) to yield 50 mg (79%) of the titled compound. ESI-MS m/z 374 ($MH^+$), 372 ($M-H^-$).

D. [5-(4-Fluorophenylcarbamoyl)pyrimidin-2-yloxy] acetic acid 2,6-dimethyl-pyridin-3-yl ester A mixture of [5-(4-fluorophenylcarbamoyl)pyrimidin-2-yloxy]acetic acid methyl ester (prepared above, 50 mg, 0.17 mmol), 2,6-dimethyl-pyridin-3-ol (21 mg, 0.17 mmol) and DMAP (41 mg, 0.34 mmol) were slurried in dichloromethane. The solution was treated with (3-dimethylamino-propyl)-ethyl-carbodiimide (EDC) (54 mg, 0.28 mmol). After 1 h, thin layer chromatography indicated complete conversion. The reaction mixture was quenched with 10 mL 1 M $HCl_{(aq)}$ and 30 mL dichloromethane. The phases were partitioned, and the aqueous phase extracted with 5 mL dichloromethane. The organic phases were combined and sequentially washed with 10 mL portions of 0.1 M $HCl_{(aq)}$, saturated. $NaHCO_{3(aq)}$ and brine. The organic layer was dried using $Na_2SO_4$, filtered and concentrated. The resulting 31 mg of off-white solid was chromatographed over $SiO_2$ (5% methanol/dichloromethane) to yield 21 mg (31%) of the titled compound. ESI-MS z/z 397 ($MH^+$), 395 ($M-H^-$).

E. The following compounds were also prepared using [5-(4-fluorophenylcarbamoyl)pyrimidin-2-yloxy]acetic acid, essentially according to the procedures of described above, using the indicated alcohol to provide the corresponding ester.

1. [5-(4-Fluorophenylcarbamoyl)pyrimidin-2-yloxy] acetic acid 2-(2,5-dimethylpyrrol-1-yl)pyridin-3-yl ester The titled compound was prepared from [5-(4-fluorophenylcarbamoyl)pyrimidin-2-yloxy]acetic acid using 2-(2,5-dimethylpyrrol-1-yl)pyridin-3-ol (32 mg, 0.17 mmol) as the source alcohol. Chromatographic (30–40% ethyl acetate/hexane) purification yielded 22 mg (28%) of the titled compound. ESI-MS t/z 462 ($MH^+$), 460 ($M-H^-$).

2. 3-{2-[5-(4-Fluorophenylcarbamoyl)pyrimidin-2-yloxy]acetoxy}-5-methoxy-1-methyl-1H-indole-2-carboxylic acid methyl ester The titled compound was prepared from [5-(4-fluorophenylcarbamoyl)pyrimidin-2-yloxy]acetic acid using 3-hydroxy-5-methoxy-1-methyl-1H-indole-2-carboxylic acid methyl ester (40 mg, 0.17 mmol) as the source alcohol. Chromatography (1:1 ethyl acetate:hexane) through $SiO_2$ yielded 13 mg (15%) of the titled compound. ESI-MS m/z 509 ($MH^+$), 507 ($M-H^-$).

3. [5-(4-Fluorophenylcarbamoyl)pyrimidin-2-yloxy] acetic acid 7-isopropyl-3-methyl-5,9-dihydro-6,8-dioxa-2-aza-benzocyclohepten-4-yl ester The titled compound was prepared from [5-(4-fluorophenylcarbamoyl)pyrimidin-2-yloxy]acetic acid using 7-isopropyl-3-methyl-5,9-dihydro-6,8-dioxa-2-aza-benzocyclohepten-4-ol (30 mg, 0.14 mmol) as the source alcohol. Chromatography (5% methanol/dichloromethane) through $SiO_2$ yielded 53 mg (63%) of the titled compound. ESI-MS m/z 497 ($MH^+$), 495 ($M-H^-$).

4. 3-{2-[5-(4-Fluorophenylcarbamoyl)pyrimidin-2-yloxy]acetoxy}-thiophene-2-carboxylic acid methyl ester The titled compound was prepared from [5-(4-fluorophenylcarbamoyl)pyrimidin-2-yloxy]acetic acid using 3-hydroxy-thiophene-2-carboxylic acid methyl ester (20 mg, 0.13 mmol) as the source alcohol. Chromatography (5% methanol/dichloromethane) through $SiO_2$ yielded 32 mg (44%) of the titled compound. ESI-MS m/z 432 ($MH^+$), 430 ($M-H^-$).

5. [5-(4-Fluorophenylcarbamoyl)pyrimidin-2-yloxy] acetic acid tert-butyl ester

The titled compound was prepared from [5-(4-fluorophenylcarbamoyl)pyrimidin-2-yloxy]acetic acid using tert-butyl alcohol (9.6 mg, 0.13 mmol) as the source alcohol. Chromatography (1:1 ethyl acetate:hexane) through $SiO_2$ yielded 5 mg (8%) of the titled compound. ESI-MS m/z 348 ($MH^+$), 346 ($M-H^-$).

6. [5-(4-Fluorophenylcarbamoyl)pyrimidin-2-yloxy] acetic acid 2,4-dimethyl-phenyl ester The titled compound was prepared from [5-(4-fluorophenylcarbamoyl)pyrimidin-2-yloxy]acetic acid using 2,4-dimethylphenol (16 mg, 0.13 mmol) as the source alcohol. Chromatography (5% methanol/dichloromethane) through $SiO_2$ yielded 48 mg (71%) of the titled compound as a white solid. ESI-MS m/z 396 ($MH^+$), 394 ($M-H^-$).

7. [5-(4-Fluorophenylcarbamoyl)pyrimidin-2-yloxy] acetic acid pyridin-3-yl ester The titled compound was prepared from [5-(4-fluorophenylcarbamoyl)pyrimidin-2-yloxy]acetic acid using 3-hydroxypyridine (12 mg, 0.13 mmol) as the source alcohol. Chromatography (5% methanol/dichloromethane) through $SiO_2$ yielded 9 mg (14%) of the titled compound. ESI-MS m/z 391 ($M+Na^+$), 367 ($M-H^-$).

8. [5-(4-Fluorophenylcarbamoyl)pyrimidin-2-yloxy] acetic acid isopropyl ester

The titled compound was prepared from [5-(4-fluorophenylcarbamoyl)pyrimidin-2-yloxy]acetic acid using isopropanol (100 µL, 1.3 mmol) as the coupling partner. Concentration (no chromatography) yielded 52 mg (92%) of the titled compound.

9. [5-(4-Fluorophenylcarbamoyl)pyrimidin-2-yloxy] acetic acid phenyl ester

The titled compound was prepared from [5-(4-fluorophenylcarbamoyl)pyrimidin-2-yloxy]acetic acid using phenol (10 mg, 0.1 mmol) as the coupling partner. Chromatography (1:1 ethyl acetate:hexane) through $SiO_2$ yielded 26 mg (42%) of the titled compound. ESI-MS m/z 368 ($MH^+$), 366 ($M-H^-$).

10. [5-(4-Fluorophenylcarbamoyl)pyrimidin-2-yloxy]acetic acid 4-nitro-phenyl ester The titled compound was prepared from [5-(4-fluorophenylcarbamoyl)pyrimidin-2-yloxy]acetic acid using p-nitrophenol (18 mg, 0.13 mmol) as the coupling partner. Chromatography (1:1 ethyl aceate:dichloromethane) through $SiO_2$ yielded 11 mg (16%) of the titled compound. ESI-MS m/z 413 ($MH^+$), 411 ($M-H^-$).

11. [5-(4-Fluorophenylcarbamoyl)pyrimidin-2-yloxy]acetic acid cyclopentyl ester The titled compound was prepared from [5-(4-fluorophenylcarbamoyl)pyrimidin-2-yloxy]acetic acid using cyclopentanol (31 μL, 0.34 mmol) as the coupling partner. Chromatography (1:1 methanol:dichloromethane) through $SiO_2$ yielded 47 mg (77%) of the titled compound as fine white needles. ESI-MS m/z 360 ($MH^+$), 358 ($M-H^-$).

12. [5-(4-Fluorophenylcarbamoyl)pyrimidin-2-yloxy]acetic acid cyclobutylmethyl ester The titled compound was prepared from [5-(4-fluorophenylcarbamoyl)pyrimidin-2-yloxy]acetic acid using cyclobutanemethanol (32 μL, 0.34 mmol) as the coupling partner. Chromatography (1:1 methanol:dichloromethane) through $SiO_2$ yielded 56 mg (92%) of the titled compound. ESI-MS m/z 360 ($MH^+$), 358 ($M-H^-$).

13. [5-(4-Fluorophenylcarbamoyl)pyrimidin-2-yloxy]acetic acid cyclopropylmethyl ester The titled compound was prepared from [5-(4-fluorophenylcarbamoyl)pyrimidin-2-yloxy]acetic acid using cyclopropanemethanol (28 μL, 0.34 mmol) as the coupling partner. Chromatography (1:1 methanol:dichloromethane) through $SiO_2$ yielded 49 mg (83%) of the titled compound as a white solid. ESI-MS m/z 346 ($MH^+$), 344 ($M-H^-$).

14. [5-(4-Fluorophenylcarbamoyl)pyrimidin-2-yloxy]acetic acid pentafluorophenylmethyl ester The titled compound was prepared from [5-(4-fluorophenylcarbamoyl)pyrimidin-2-yloxy]acetic acid using pentafluorophenol (30 mg, 0.15 mmol) as the coupling partner. Chromatography (1:1 methanol:dichloromethane) through $SiO_2$ yielded 70 mg (87%) of the titled compound. ESI-MS m/z 472 ($MH^+$), 470 ($M-H^-$).

15. [5-(4-Fluorophenylcarbamoyl)pyrimidin-2-yloxy]acetic acid phenethyl ester The titled compound was prepared from [5-(4-fluorophenylcarbamoyl)pyrimidin-2-yloxy]acetic acid using 2-phenyl-ethanol (18 mg, 0.15 mmol) as the coupling partner. Chromatography (1:1 methanol:dichloromethane) through $SiO_2$ yielded 49 mg (73%) of the titled compound. ESI-MS m/z 396 ($MH^+$), 394 ($M-H^-$).

16. 2-{2-[4-(4-Bromophenyl)-4-hydroxy-piperidin-1-yl]-2-oxo-ethoxy}-pyrimidine-5-carboxylic acid (4-fluorophenyl)amide The titled compound was prepared from [5-(4-fluorophenylcarbamoyl)pyrimidin-2-yloxy]acetic acid using 4-(4-bromophenyl)-piperidin-4-ol (56 mg, 0.22 mmol) as the coupling partner. Concentration (no chromatography) yielded 76 mg (84%) of the titled compound. ESI-MS m/z 530, 532 ($MH^+$), 527, 529 ($M-H^-$).

17. [5-(4-Fluorophenylcarbamoyl)pyrimidin-2-yloxy]acetic acid 3-dimethylamino-phenyl ester The titled compound was prepared from [5-(4-fluorophenylcarbamoyl)pyrimidin-2-yloxy]acetic acid using 3-dimethylaminophenol (21 mg, 0.15 mmol) as the coupling partner. Concentration (no chromatography) yielded 53 mg (76%) of the titled compound as a pink-purple solid. ESI-MS m/z 411 ($MH^+$), 409 ($M-H^-$).

18. [5-(4-Fluorophenylcarbamoyl)pyrimidin-2-yloxy]acetic acid 3,3-dimethyl-butyl ester The titled compound was prepared from [5-(4-fluorophenylcarbamoyl)pyrimidin-2-yloxy]acetic acid using 3,3-dimethylbutanol (26 mg, 0.26 mmol) as the coupling partner. Concentration (no chromatography) yielded 54 mg (85%) of the titled compound. ESI-MS m/z 376 ($MH^+$), 374 ($M-H^-$).

19. [5-(4-Fluorophenylcarbamoyl)pyrimidin-2-yloxy]acetic acid 2-cyclohexyloxy-ethyl ester The titled compound was prepared from [5-(4-fluorophenylcarbamoyl)pyrimidin-2-yloxy]acetic acid using 2-cyclohexyloxy-ethanol (37 mg, 0.26 mmol) as the coupling partner. Chromatography (1:1 ethyl acetate:dichloromethane) through $SiO_2$ yielded 36 mg (51%) of the titled compound. ESI-MS m/z 418 ($MH^{30}$), 416 ($M-H^-$).

20. [5-(4-Fluorophenylcarbamoyl)pyrimidin-2-yloxy]acetic acid 2-fluorophenyl ester The titled compound was prepared from [5-(4-fluorophenylcarbamoyl)pyrimidin-2-yloxy]acetic acid using 2-fluorophenol (17 mg, 0.15 mmol) as the coupling partner. Concentration (no chromatography) yielded 11 mg (17%) of the titled compound. ESI-MS m/z 386 ($MH^+$), 384 ($M-H^-$).

21. [5-(4-Fluorophenylcarbamoyl)pyrimidin-2-yloxy]acetic acid 4-fluorophenyl ester The titled compound was prepared from [5-(4-fluorophenylcarbamoyl)pyrimidin-2-yloxy]acetic acid using 4-fluorophenol (17 mg, 0.15 mmol) as the coupling partner. Concentration (no chromatography) yielded 52 mg (79%) of the titled compound. ESI-MS m/z 386 ($MH^+$), 384 ($M-H^-$).

22. [5-(4-Fluorophenylcarbamoyl)pyrimidin-2-yloxy]acetic acid 2-adamantan-1-yl-ethyl ester The titled compound was prepared from [5-(4-fluorophenylcarbamoyl)pyrimidin-2-yloxy]acetic acid using 1-adamantaneethanol (27 mg, 0.15 mmol) as the coupling partner.

Concentration (no chromatography) yielded 58 mg (75%) of the titled compound. ESI-MS m/z 454 (MH$^+$), 452 (M–H$^-$).

23. [5-(4-Fluorophenylcarbamoyl)pyrimidin-2-yloxy]acetic acid cycloheptyl ester The titled compound was prepared from [5-(4-fluorophenylcarbamoyl)pyrimidin-2-yloxy]acetic acid using cycloheptanol (39 mg, 0.34 mmol) as the coupling partner. Concentration (no chromatography) yielded 53 mg (80%) of the titled compound. ESI-MS m/z 388 (MH$^+$), 386 (M–H$^-$).

24. [5-(4-Fluorophenylcarbamoyl)pyrimidin-2-yloxy]acetic acid 5-phenyl-pentyl ester The titled compound was prepared from [5-(4-fluorophenylcarbamoyl)pyrimidin-2-yloxy]acetic acid using 5-phenyl-1-pentanol (56 mg, 0.34 mmol) as the coupling partner. Chromatography (gradient 5–95% ethyl acetate/hexane) through SiO$_2$ yielded 6 mg (28%) of the titled compound. ESI-MS m/z 438 (MH$^+$), 436 (M–H$^-$).

F. The following compounds were also prepared using [5-(4-fluorophenylcarbamoyl)-pyrimidin-2-yloxy]acetic acid, essentially according to the procedures of described above, however instead of using an alcohol, an amine was utilized as the coupling partner so as to provide the corresponding amide.

1. 2-Dimethylcarbamoylmethoxypyrimidine-5-carboxylic acid (4-fluorophenyl)amide The titled compound was prepared from [5-(4-fluorophenylcarbamoyl)pyrimidin-2-yloxy]acetic acid using 40% aqueous dimethylamine (25 µL, 0.19 mmol) as the coupling partner. Chromatography (10% methanol/dichloromethane) through SiO$_2$ yielded 14 mg (26%) of the titled compound. ESI-MS m/z 319 (MH$^+$), 317 (M–H$^-$).

2. 2-Phenylcarbamoylmethoxypyrimidine-5-carboxylic acid (4-fluorophenyl)amide The titled compound was prepared from [5-(4-fluorophenylcarbamoyl)pyrimidin-2-yloxy]acetic acid using aniline (12 mg, 0.13 mmol) as the coupling partner. Chromatography (10% methanol/dichloromethane) through SiO$_2$ yielded 14 mg (22%) of the titled compound. ESI-MS m/z 367 (MH$^+$), 365 (M–H$^-$).

3. 2-(Benzylcarbamoylmethoxy)pyrimidine-5-carboxylic acid (4-fluorophenyl)amide The titled compound was prepared from [5-(4-fluorophenylcarbamoyl)pyrimidin-2-yloxy]acetic acid using benzylamine (20 µL, 0.21 mmol) as the coupling partner. Concentration (no chromatography) yielded 58 mg (90%) of the titled compound. ESI-MS m/z 381 (MH$^+$), 379 (M–H$^-$).

4. 2-[(2,4-Difluorophenylcarbamoyl)methoxy]pyrimidine-5-carboxylic acid (4-fluorophenyl)amide The titled compound was prepared from [5-(4-fluorophenylcarbamoyl)pyrimidin-2-yloxy]acetic acid using 1,4-difluoroaniline (20 µL, 0.20 mmol) as the coupling partner. Concentration (no chromatography) yielded 60 mg (88%) of the titled compound. ESI-MS m/z 403 (MH$^+$), 401 (M–H$^-$).

5. 2-(Pyridin-3-ylcarbamoylmethoxy)pyrimidine-5-carboxylic acid (4-fluorophenyl)amide The titled compound was prepared from [5-(4-fluorophenylcarbamoyl)pyrimidin-2-yloxy]acetic acid using 3-aminopyridine (20 mg, 0.21 mmol) as the coupling partner. Concentration (no chromatography) yielded 17 mg (27%) of the titled compound. ESI-MS m/z 368 (MH$^+$), 366 (M–H$^-$).

6. 2-[(Methylphenylcarbamoyl)methoxy]pyrimidine-5-carboxylic acid (4-fluorophenyl)amide The titled compound was prepared from [5-(4-fluorophenylcarbamoyl)pyrimidin-2-yloxy]acetic acid using N-methylaniline (23 µL, 0.21 mmol) as the coupling partner. Concentration (no chromatography) yielded 45 mg (70%) of the titled compound. ESI-MS m/z 381 (MH$^+$), 379 (M–H$^-$).

7. 2-Cyclohexylcarbamoylmethoxypyrimidine-5-carboxylic acid (4-fluorophenyl)amide The titled compound was prepared from [5-(4-fluorophenylcarbamoyl)pyrimidin-2-yloxy]acetic acid using cyclohexylamine (24 µL, 0.21 mmol) as the coupling partner. Concentration (no chromatography) yielded 36 mg (57%) of the titled compound. ESI-MS m/z 373 (MH$^+$), 371 (M–H$^-$).

8. 2-[(4-Nitrophenylcarbamoyl)methoxy]pyrimidine-5-carboxylic acid (4-fluorophenyl)amide The titled compound was prepared from [5-(4-fluorophenylcarbamoyl)pyrimidin-2-yloxy]acetic acid using 4-nitroaniline (25 mg, 0.18 mmol) as the coupling partner. Chromatography (5% methanol/dichloromethane) through SiO$_2$ yielded 13 mg (23%) of the titled compound. ESI-MS m/z 412 (MH$^+$), 410 (M–H$^-$).

9. 2-(Bicyclo[2.2.1]hept-2-ylcarbamoylmethoxy)pyrimidine-5-carboxylic acid (4-fluorophenyl)amide The titled compound was prepared from [5-(4-fluorophenylcarbamoyl)pyrimidin-2-yloxy]acetic acid using 2-aminonorbornane (21 µL, 0.18 mmol) as the coupling partner. Concentration (no chromatography) yielded 38 mg (71%) of the titled compound. ESI-MS m/z 385 (MH$^+$), 383 (M–H$^-$).

10. 2-{[(Naphthalen-1-ylmethyl)carbamoyl]methoxy}pyrimidine-5-carboxylic acid (4-fluorophenyl)amide The titled compound was prepared from [5-(4-fluorophenylcarbamoyl)pyrimidin-2-yloxy]acetic acid using naphthylenemethylamine (28 mg, 0.18 mmol) as the coupling partner. Concentration (no chromatography) yielded 43 mg (71%) of the titled compound. ESI-MS m/z 431 (MH$^+$), 429 (M–H$^-$).

11. 2-[(3-Butylsulfamoylphenylcarbamoyl)methoxy]pyrimidine-5-carboxylic acid (4-fluorophenyl)amide The titled compound was prepared from [5-(4-fluorophenylcarbamoyl)pyrimidin-2-yloxy]acetic acid using 3-amino-N-butyl-benzenesulfonamide (53 mg, 0.21 mmol) as the coupling partner. Chromatography (1:1 ethyl acetate:dichloromethane) through SiO$_2$ yielded 23 mg (27%) of the titled compound. ESI-MS m/z 502 (MH$^+$), 500 (M−H$^−$).

EXAMPLE 4

Synthesis of 2-[(Methoxymethylcarbamoyl)methoxy]-pyrimidine-5-carboxylic acid (4-fluorophenyl) amide A mixture of [5-(4-fluorophenylcarbamoyl)pyrimidin-2-yloxy]acetic acid methyl ester (prepared as in Example 3, 100 mg, 0.34 mmol), dimethylhydroxylamine hydrochloride (40 mg, 0.41 mmol) and DMAP (82 mg, 0.68 mmol) were slurried in dichloromethane. The solution was treated with (3-dimethylaminopropyl)ethylcarbodiimide (EDC) (54 mg, 0.28 mmol). After 19 h, LC/MS indicated complete conversion. Reaction was quenched with 30 mL 1 M NH$_4$Cl$_{(aq)}$ and 50 mL dichloromethane. The phases were partitioned and the organic layer was sequentially washed with 30 mL portions of 0.1 M NH$_4$Cl$_{(aq)}$, saturated NaHCO$_{3(aq)}$ and brine. The organic layer was dried using Na$_2$SO$_4$, filtered and concentrated to yield 101 mg (89%) of the titled compound as a white solid. ESI-MS m/z 335 (MH$^+$), 333 (M−H$^−$).

EXAMPLE 5

Synthesis of 2-(2-Oxobutoxy)pyrimidine-5-carboxylic acid (4-fluorophenyl)amide

2-[(Methoxymethylcarbamoyl)methoxy]pyrimidine-5-carboxylic acid (4-fluorophenyl)amide (prepared as in Example 4, 60 mg, 0.18 mmol) was suspended in 1.8 mL THF and cooled to 0° C. Ethyl magnesium bromide (1 M in THF, 0.45 mL, 0.45 mmol) was added dropwise while maintaining internal reaction temperature between 0° C. and 5° C. The reaction mixture was warmed to ambient temperature and held for 1 h. The reaction mixture was cooled back to 0° C. and a second addition (0.45 mL, 0.45 mmol) of Grignard reagent was performed. The reaction was warmed to ambient temperature and held for 2.5 hours. The reaction was quenched with 0.1 M HCl and diluted with ethyl acetate. The organic layer was separated, dried using Na2SO4 and concentrated to 36 mg of yellow oil. The crude material was purified by SiO2 chromatography to deliver 8 mg (15% yield) of the titled compound. ESI-MS m/z 304 (MH+), 302 (M−H−).

EXAMPLE 6

Resin-bound glycolate preparation and Uses

Resin-Bound Glycolate

A suspension consisting of 4-hydroxyphenylsulfonylmethyl polystyrene (500 mg, 0.525 meq) and [5-(4-fluorophenylcarbamoyl)pyrimidin-2-yloxy]acetic acid (306 mg, 1.05 mmol) and DMAP (128 mg, 1.05 mmol) in DMF (5 mL) was treated dropwise with DIC (0.16 mL, 1.05 mmol) at ambient temperature. After 21.5 h, the resin was filtered over sintered glass, and then washed sequentially with 5×10 mL DMF, 5×10 mL 1:1 DMF:dichloromethane, and 5×10 mL dichloromethane. Residual solvent was removed in vacuo, resulting in 600 mg isolated product that was used without further purification to prepare the following products.

A. 2-[2-(4-Methylpiperazin-1-yl)-2-oxoethoxy]pyrimidine-5-carboxylic acid (4-fluorophenyl)amide A suspension of 114 mg of the resin-bound glycolate (<85 µmol) in 1.0 mL DMF was treated with 1-methylpiperizine (7.5 mg, 75 µmol) at 50° C. After 3 days, the reaction mixture was diluted with dichloromethane and filtered. The resin was rinsed with 3×15 mL dichloromethane. The filtrates were combined and concentrated to dryness. Chromatography (10–20% methanol/dichloromethane) through SiO$_2$ yielded 8 mg (25%) of the titled compound. ESI-MS m/z 374 (MH$^+$), 372 (M−H$^−$).

B. 2-Cyclopentylcarbamoylmethoxypyrimidine-5-carboxylic acid (4-fluorophenyl)amide A suspension of 89 mg of the resin-bound glycolate in 1.5 mL pyridine was treated with cyclopentylamine (10 µL, 100 µmol) at 50° C. After 2 days, the reaction mixture was diluted with dichloromethane and filtered. The resin was rinsed with 3×15 mL dichloromethane. The filtrates were combined and concentrated to dryness. Chromatography (gradient 2–10% methanol/dichloromethane) through SiO$_2$ yielded 7 mg of the titled compound. ESI-MS m/z 359 (MH$^+$), 357 (M−H$^−$).

C. 2-[(4-Methoxyphenylcarbamoyl)methoxy]pyrimidine-5-carboxylic acid (4-fluorophenyl)amide A suspension of 200 mg of the resin-bound glycolate in acetic acid (1.0 mL) was treated with 30% H$_2$O$_2$ (420 µL, 4.1 mmol). After 5 hours, the reaction mixture was diluted with dichloromethane and filtered. The resin was rinsed with copious dichloromethane and dried in vacuo. Of the recovered resin mass, 27% was then treated with p-anisidine (13 mg, 0.11 mmol) in 0.5 mL pyridine. After stirring for 2 days at 45° C., the resin was filtered over sintered glass and rinsed with pyridine and dichloromethane. Chromatography (1:1 ethyl acetate:dichloromethane) through SiO$_2$ yielded 4 mg of the titled compound. ESI-MS m/z 397 (MH$^+$), 395 (M−H$^−$).

EXAMPLE 7

Synthesis of 2-Carbamoylmethylsulfanyl-4-methylpyrimidine-5-carboxylic acid (4-fluorophenyl) amide and Oxidation Products Thereof A. A solution of 2-mercaptopyrimidine-5-carboxylic acid (4-fluorophenyl)amide (100 mg, 0.38 mmol) in 3 mL of ethanol was treated with aqueous NaOH (3 M, 0.28 mL, 0.84 mmol). A yellow slurry formed, which dissolved over the course of 5 min. An addition of 2-chloroacetamide (53 mg, 0.57 mmol) resulted in the formation of a white slurry. After stirring at ambient temperature for 2.5 h, the reaction was quenched with 50 mL of water and titrated to acidity with 1 M HCl. The slurry was filtered over sintered glass and washed with copious water. Drying in vacuo yielded 85 mg (70%) of 2-carbamoylmethylsulfanyl-4-methylpyrimidine-5-carboxylic acid (4-fluorophenyl)amide. ESI-MS m/z 321 (MH$^+$), 319 (M−H$^−$).

B. 2-Carbamoylmethylsulfinyl-4-methylpyrimidine-5-carboxylic acid (4-fluorophenyl)amide A solution of 2-carbamoylmethylsulfanyl-4-methylpyrimidine-5-carboxylic acid (4-fluorophenyl)amide (77 mg, 0.24 mmol) and m-CPBA (64 mg, 0.37 mmol) in 2 mL of dichloromethane was stirred at ambient temperature for 16 h. The reaction was concentrated in vacuo and chromatographed through $SiO_2$ (5–10% methanol/dichloromethane), to afford 53 mg (66% yield) of the titled product. ApcI-MS m/z 337 ($MH^+$).

C. 2-Carbamoylmethanesulfonyl-4-methylpyrimidine-5-carboxylic acid (4-fluorophenyl)amide A solution of 2-carbamoylmethylsulfinyl-4-methylpyrimidine-5-carboxylic acid (4-fluorophenyl)amide (as prepared above, 42 mg, 0.12 mmol) and m-CPBA (47 mg, 0.27 mmol) in 2 mL of 1:1 dichloromethane:DMF was stirred at ambient temperature for 3 days. The solution was diluted with 40 mL of 1:1 ethyl acetate:hexane and sequentially washed with 2×10 mL 5% $NaHCO_{3(aq)}$, 10 mL 0.1 M $HCl_{(aq)}$ and 10 mL brine. The organic layer was dried using $Na_2SO_4$ and concentrated to a white solid which was triturated with 10 mL of 1:1 dichloromethane:hexane, yielding 8 mg (19%) of the titled compound as a white solid.

EXAMPLE 8

Synthesis of 4-Methyl-2-(2-oxo-2-phenylethanesulfonyl)pyrimidine-5-carboxylic acid (4-fluorophenyl)amide A solution of sodium 5-(4-fluorophenylcarbamoyl)pyrimidine-2-sulfinate (76 mg, 0.24 mmol) in 2 mL of DMF was treated with 2-bromoacetophenone (48 mg, 0.24 mmol) and stirred at ambient temperature for 3 days. The solution was then diluted with 15 mL ethyl acetate and 5 mL hexane and sequentially washed with 2×5 mL portions of 0.1 M HCl and 5 mL of water. The organic phase was dried using $Na_2SO_4$, concentrated and the resultant oil chromatographed through $SiO_2$ (2–5% MeOH/dichloromethane). Recrystallization in ethyl acetate/hexane yielded 26 mg (27%) of the titled compound as yellowish needles. ApcI-MS m/z 414 ($MH^+$), 412 ($M-H^-$).

EXAMPLE 9

Synthesis of [4-Amino-5-(4-fluorophenylcarbamoyl)pyrimidin-2-ylsulfanyl]acetic acid ethyl ester

A. Potassium-4-amino-2-tritylsulfanylpyrimidine-5-carboxylate

Solid portions of $Na_2CO_3$ (3.7 g, 25 mmol) followed by triphenylmethylchloride (6.4 g, 23 mmol) were added, at ambient temperature, to a stirred solution of ethyl-4-amino-2-mercapto-pyrimidine-5-carboxylate (Lancaster; 5.0 g, 25 mmol) in DMSO (100 mL). After 30 min, the resulting suspension was diluted with $H_2O$ (500 mL) and extracted with dichloromethane (5×100 mL). The combined organic extract was washed with $H_2O$ (2×100 mL), dried using $Na_2SO_4$ and diluted with THF (100 mL). Solid KOTMS (90% tech., 7.4 g, 60 mmol) was immediately added to this solution of crude trityl protected sulfide and the resulting yellow suspension was stirred at reflux (1 h). After allowing to cool to ambient temperature, the resulting voluminous white solids were collected by filtration, washed with dichloromethane and dried in vacuo to afford the titled compound (8.0 g, 18 mmol, 78% yield): $^1$H NMR (300 MHz, DMSO-$d_6$) δ 7.95 (s, 1H), 7.29–7.13 (m, 18H).

B. 4-Amino-2-mercaptopyrimidine-5-carboxylic acid (4-fluorophenyl)amide

Solid portions of potassium-4-amino-2-tritylsulfanylpyrimidine-5-carboxylate (46 g, 10 mmol) followed by HATU (39 g, 0.10 mol) were added, at ambient temperature, to a solution of 4-fluoroaniline (11 g, 0.10 mol) and NMM (31 g, 0.30 mol) in NMP (500 mL). After stirring for 12 hours, the resulting orange solution was poured into water (1000 mL) and the oily, solid precipitant was collected, dissolved in dichloromethane (500 mL), and diluted with acetic acid (50 mL). The resulting solution was stirred (ambient temperature, 3 h), then concentrated in vacuo (to about 150 mL total volume) and diluted with diethyl ether (100 mL). The resulting yellow solid was collected, washed with dichloromethane and dried in vacuo to afford the titled compound (13 g, 49 mmol, 49% yield). $^1$H NMR (300 MHz, $CD_3OD$) δ 8.20 (s, 1H), 7.58 (dd, J=9.3, 4.8 Hz, 2H), 7.07 (app. t, J=9.0 Hz, 2H); MS (+APCI) m/z 265 (MH+, 100).

C. [4-Amino-5-(4-fluorophenylcarbamoyl)pyrimidin-2-ylsulfanyl]acetic acid ethyl ester A solution of ethyl bromoacetate (0.128 g, 0.76 mmol) in acetone (2 mL) was added to a suspension of 4-amino-2-mercaptopyrimidine-5-carboxylic acid (4-fluorophenyl) amide (0.10 g, 0.38 mmol) and $Na_2CO_3$ (80 mg, 0.76 mmol) in acetone (5 mL). After stirring at ambient temperature for 2 hours, the resulting suspension was filtered and the filtrate concentrated to afford a crude solid that was recrystallized in dichloromethane/hexanes, or alternatively $CH_3CN/H_2O$) to afford the titled compound as a white solid (100 mg, 0.29 mmol, 76% yield). $^1$H NMR (300 MHz, $d_6$-acetone) δ 9.60 (bs, 1H), 8.67 (s, 1H), 7.75 (m, 1H), 7.56 (m, 2H), 4.15 (m, 2H), 3.92 (s, 1H), 1.22 (m, 3H).

D. The following compounds were synthesized in a manner similar to [4-amino-5-(4-fluorophenylcarbamoyl)pyrimidin-2-ylsulfanyl]acetic acid ethyl ester as described above:

[4-Amino-5-(4-fluorophenylcarbamoyl)pyrimidin-2-ylsulfanyl]acetic acid benzyl ester: $^1$H NMR (300 MHz, $d_6$-acetone) δ 9.62 (s, 1H), 8.63 (s, 1H), 7.78 (m, 2H), 7.55 (s, 2H), 7.36 (m, 5H), 7.20 (m, 2H), 5.08 (s, 2H), 4.01 (s, 2H).

[4-Amino-5-(4-fluorophenylcarbamoyl)pyrimidin-2-ylsulfanyl]acetic acid: $^1$H NMR (300 MHz, $d_6$-acetone) δ 9.78 (bs, 1H), 9.02 (bs, 1H), 8.44 (bs, 1H), 7.90 (bs, 1H), 7.75 (m, 2H), 7.10 (m, 1H), 3.96 (s, 2H).

3-[4-Amino-5-(4-fluorophenylcarbamoyl)pyrimidin-2-ylsulfanylmethyl]benzoic acid: MS (EI) m/z 397.11 ($M-H^-$).

[4-Amino-5-(4-fluorophenylcarbamoyl)pyrimidin-2-ylsulfanyl]acetic acid 4-nitro-benzyl ester: MS (EI) m/z 456.15 ($M-H^-$).

[4-Amino-5-(4-fluorophenylcarbamoyl)pyrimidin-2-ylsulfanyl]acetic acid allyl ester: MS (EI) m/z 361.09 ($M-H^-$).

[4-Amino-5-(4-fluorophenylcarbamoyl)pyrimidin-2-ylsulfanyl]acetic acid tert-butyl ester: MS (EI) m/z 379 ($M-H^-$).

4-Amino-2-(benzylcarbamoyl-methylsulfanyl)pyrimidine-5-carboxylic acid (4-fluorophenyl)amide: MS (EI) m/z 412.11 ($M+H^+$).

2-Allylcarbamoylmethylsulfanyl-4-aminopyrimidine-5-carboxylic acid (4-fluorophenyl)amide: MS (EI) m/z 360.21 ($M-H^-$).

[4-Amino-5-(3,4-difluorobenzylcarbamoyl)pyrimidin-2-yl-sulfanyl]acetic acid benzyl ester: $^1$H NMR (300 MHz, d$_6$-acetone) δ 8.58 (s, 1H), 8.45 (s, 1H), 7.35–7.18 (m, 8H), 5.16 (s, 1H), 4.54 (m, 2H), 4.00 (s, 2H).

[4-Amino-5-(4-fluorophenylcarbamoyl)pyrimidin-2-ylsulfanyl]acetic acid methyl ester: MS (EI) m/z 335 (M–H)$^-$.

4-Amino-2-(2-oxo-butylsulfanyl)pyrimidine-5-carboxylic acid (4-fluorophenyl)amide: MS (EI) m/z 333 (M–H)$^-$.

3-[4-Amino-5-(4-fluorophenylcarbamoyl)pyrimidin-2-yl-sulfanyl]propionic acid ethyl ester: MS (EI) m/z 363 (M–H)$^-$.

4-[4-Amino-5-(4-fluorophenylcarbamoyl)pyrimidin-2-yl-sulfanyl]butyric acid ethyl ester: MS (EI) m/z 379 (M+H)$^+$.

[4-Amino-5-(4-fluorophenylcarbamoyl)pyrimidin-2-ylsulfanyl]acetic acid propyl ester: MS (EI) m/z 296.2 (M–H)$^-$.

[4-Amino-5-(4-fluorophenylcarbamoyl)pyrimidin-2-ylsulfanyl]acetic acid 4-chloro-benzyl ester: MS (EI) m/z 445 (M–H)$^-$.

[4-Amino-5-(4-fluorophenylcarbamoyl)pyrimidin-2-ylsulfanyl]acetic acid 2-naphthalen-1-yl-ethyl ester: MS (EI) m/z 477 (M+H)$^+$.

[4-Amino-5-(4-fluorophenylcarbamoyl)pyrimidin-2-ylsulfanyl]acetic acid biphenyl-4-ylmethyl ester: MS (EI) m/z 489 (M+H)$^+$.

[4-Amino-5-(4-fluorophenylcarbamoyl)pyrimidin-2-ylsulfanyl]acetic acid 2-methyl-biphenyl-3-ylmethyl ester: MS (EI) m/z 501 (M–H)$^-$.

[4-Amino-5-(4-fluorophenylcarbamoyl)pyrimidin-2-ylsulfanyl]acetic acid biphenyl-2-ylmethyl ester: MS (EI) m/z 489 (M+H)$^+$.

[4-Amino-5-(4-fluorophenylcarbamoyl)pyrimidin-2-ylsulfanyl]acetic acid naphthalen-1-ylmethyl ester: MS (EI) m/z 461 (M–H)$^-$.

[4-Amino-5-(4-fluorophenylcarbamoyl)pyrimidin-2-ylsulfanyl]acetic acid 3-phenoxy-benzyl ester: MS (EI) m/z 503 (M–H)$^-$.

[4-Amino-5-(4-fluorophenylcarbamoyl)pyrimidin-2-ylsulfanyl]acetic acid 3,5-dimethoxy-benzyl ester: MS (EI) m/z 471 (M–H)$^-$.

4-{2-[4-Amino-5-(4-fluorophenylcarbamoyl)pyrimidin-2-ylsulfanyl]acetoxymethyl}-benzoic acid methyl ester: MS (EI) m/z 469 (M–H)$^-$.

5-{2-[4-Amino-5-(4-fluorophenylcarbamoyl)pyrimidin-2-ylsulfanyl]acetoxymethyl}-isophthalic acid diethyl ester: MS (EI) m/z 555 (M–H)$^-$.

[4-Amino-5-(4-fluorophenylcarbamoyl)pyrimidin-2-ylsulfanyl]acetic acid pentafluorophenylmethyl ester: MS (EI) m/z 519 (M–H)$^-$.

[4-Amino-5-(4-fluorophenylcarbamoyl)pyrimidin-2-ylsulfanyl]acetic acid 2,4,6-trimethyl-benzyl ester: MS (EI) m/z 453 (M–H)$^-$.

[4-Amino-5-(4-fluorophenylcarbamoyl)pyrimidin-2-ylsulfanyl]acetic acid 9H-fluoren-9-yl ester: MS (EI) m/z 485 (M–H)$^-$.

[4-Amino-5-(4-fluorophenylcarbamoyl)pyrimidin-2-yloxy]acetic acid benzyl ester: MS (EI) m/z 395 (M–H)$^-$.

4-Amino-2-[3-(2-chloro-phenylcarbamoyl)-2-oxo-propyl-sulfanyl]pyrimidine-5-carboxylic acid (4-fluorophenyl)amide: MS (EI) m/z 472 (M–H)$^-$.

EXAMPLE 10

Compounds prepared from 4-chloro-2-methylsulfanylpyrimidine-5-carboxylic acid (4-fluorophenyl)amide

A. 4-Chloro-2-methylsulfanylpyrimidine-5-carbonyl chloride

A slurry of potassium trimethylsilyl oxide (90% tech., 40 g, 0.31 mol) in 1,2-dimethoxyethane (300 mL) was added, slowly over 20 min, to a solution of ethyl-4-chloro-2-methylthio-5-pyrimidinecarboxylate (Aldrich, 15 g, 64 mmol) in 1,2-dimethoxyethane (100 mL). Said addition, being mildly exothermic, may warrant the use of an ice bath to maintain ambient temperature conditions during addition. After addition was complete, the resulting suspension was stirred at ambient temperature for 1 h, then warmed to reflux for 36 h, then allowed to cool to ambient temperature. Reaction mixture was quenched with 1 M HCl$_{(aq)}$, then extracted with ethyl acetate and dried using sodium sulfate to produce a crude solid (11 g). Said crude solid was then recrystallized in ethyl acetate to afford 4-hydroxy-2-methylsulfanylpyrimidine-5-carboxylic acid as a white solid (8.8 g, 47 mmol, 73% yield). MS (–ESI) m/z 185 (M–, 100). An aliquot of this material (3.00 g, 16.1 mmol) was diluted with thionyl chloride (90 mL) followed by DMF (0.20 mL) and the resulting solution was warmed to reflux. After 1 hour at reflux, the solution was allowed to cool to ambient temperature and was concentrated in vacuo to afford a beige solid which was triturated once from hot toluene and then once again from hot hexanes (i.e., in both instances the soluble material was the desired fraction). This afforded, after concentration in vacuo, the titled compound as a white solid (3.90 g, 15.6 mmol, 97% yield). $^1$H NMR (300 MHz, CDCl$_3$) δ 9.15 (s, 1H), 2.63 (s, 3H).

B. 4-Chloro-2-methylsulfanylpyrimidine-5-carboxylic acid (4-fluorophenyl)amide To a mixture of 4-chloro-2-methylsulfanylpyrimidine-5-carbonyl chloride prepared above (113 mg, 0.54 mmol) in dichloromethane was added 4-fluoroaniline (56 µL, 0.59 mmol). This was followed by the dropwise addition of DIPEA. The mixture was stirred for 15 min, the mixture was diluted with dichloromethane, washed with water and saturated aqueous sodium bicarbonate and was dried over sodium sulfate. Filtration and concentration afforded a residue that was purified by trituration from ethyl acetate with hexanes. The resulting off-white solid (122 mg, 0.41 mmol, 76%) was sufficiently pure to use without further purification. $^1$H NMR (300 MHz, DMSO-d$_6$) δ 10.7 (s, 1H), 8.86 (s, 1H), 7.69 (m, 2H), 7.23 (m, 2H), 2.56 (s, 3H); MS (EI) m/z 296.2 (M–H)$^-$.

C. {2-[5-(4-Fluorophenylcarbamoyl)-2-methylsulfanylpyrimidin-4-ylamino]-ethyl}carbamic acid tert-butyl ester tert-Butyl N-(2-aminoethyl)carbamate (0.500 g, 3.12 mmol) and DIPEA (0.83 mL, 4.68 mmol, 1.5 eq) was added to a solution of 4-chloro-2-methylsulfanylpyrimidine-5-carboxylic acid (4-fluorophenyl)amide (0.929 g, 3.12 mmol) in DMF (5.0 ml) and stirred under N$_2$ overnight. The reaction mixture was diluted with ethyl acetate (50 mL) and washed twice with water (50 mL). Upon precipitation of product out of the organic layer of the mixture, the white solid was filtered, and recrystallized from hot ethyl acetate to yield 1.06 g (80%) of the titled product as a white solid. $^1$H NMR: (d$_6$-DMSO) δ 10.21 (s, 1H), 8.56 (s, 1H), 7.64 (m, 2H), 7.16 (m, 2H), 6.92 (t, 1H), 3.48 (m, 2H), 3.30 (s, 3H), 3.11 (m, 2H), 1.31 (s, 9H); HPLC: R$_t$=4.32 min; MS (ESI): m/z 419.97 (M–H)⁻.

D. {2-[5-(4-Fluorophenylcarbamoyl)-2-methylsulfonyl-pyrimidin-4-ylamino]-ethyl}-carbamic acid tert-butyl ester To a solution of {2-[5-(4-fluorophenylcarbamoyl)-2-methylsulfanylpyrimidin-4-ylamino]ethyl}carbamic acid tert-butyl ester (0.35 g, 0.8 mmol) in DMF (5.0 mL), m-CPBA (0.50 g, 2.9 mmol, 3.5 eq) was added, and stirred under N$_2$ for 4 h. The product was precipitated out of solution by pouring the reaction mixture over crushed ice. The resulting solid was re-dissolved in ethyl acetate (20 mL), then washed with water (3×10 mL), saturated NaHCO$_3$ (3×10 mL), water (3×10 mL), saturated NaCl (20 mL) and dried over MgSO$_4$. Following filtration, the solvent was removed by rotary evaporation to yield the titled product (0.31 g, 82%) as a white solid. $^1$H NMR: (d$_6$-DMSO) δ 10.53 (s, 1H), 8.79 (s, 1H), 8.73 (m, 1H), 7.67 (m, 2H), 7.20 (m, 2H), 6.97 (t, 1H), 3.50 (m, 2H), 3.32 (s, 3H), 1.29 (s, 9H); HPLC: R$_t$=4.12 min; MS (ESI): m/z 452.30 (M–H)⁻.

E. [4-(2-tert-Butoxycarbonylaminoethylamino)-5-(4-fluorophenylcarbamoyl)pyrimidin-2-ylsulfanyl]acetic acid ethyl ester Ethyl thioglycolate (73 μL, 0.66 mmol) was added to a solution of {2-[5-(4-fluorophenylcarbamoyl)-2-methylsulfonyl-pyrimidin-4-ylamino]-ethyl}carbamic acid tert-butyl ester (0.30 g, 0.66 mmol) and DIPEA (117 μL, 0.66 mmol) in DMF (1.5 mL). The resulting solution was stirred under N$_2$ overnight. The reaction mixture was then diluted with ethyl acetate (20 mL) and washed with water (10 mL), 1 N HCl (3×10 mL), water (10 mL), saturated NaHCO$_3$ (3×10 mL), water (10 mL), saturated NaCl (20 mL) and dried over MgSO$_4$. Following filtration, the solvent was removed by rotary evaporation to yield the titled product (0.19 g, 58%) as an off-white solid. $^1$H NMR: (d$_6$-DMSO) δ 10.25 (s, 1H), 8.63 (m, 1H), 8.57 (s, 1H), 7.65 (m, 2H), 7.16 (m, 2H), 6.91 (t, 1H), 4.08 (q, 2H), 3.96 (s, 2H), 3.44 (m, 2H), 3.08 (m, 2H), 1.31 (s, 9H), 1.16 (t, 3H); HPLC: R$_t$=4.41 min; MS (ESI): m/z 492.44 (M–H)⁻.

F. [4-(2-Aminoethylamino)-5-(4-fluorophenylcarbamoyl)pyrimidin-2-ylsulfanyl]acetic acid ethyl ester

[4-(2-tert-Butoxycarbonylaminoethylamino)-5-(4-fluorophenylcarbamoyl)pyrimidin-2-ylsulfanyl]acetic acid ethyl ester (113 mg, 0.23 mmol) was dissolved in a trifluoroacetic acid/dichloromethane solution (50%, 4 mL) and the resulting solution was stirred under N$_2$ for 2 h. The solvent was removed by rotary evaporation, and trituration with diethyl ether was attempted. The resulting gummy solid was dissolved in water and lyophilized to yield the titled product (102 mg, 88% as trifluoroacetic acid salt) as a hygroscopic and flocculent white solid. $^1$H NMR: (d$_6$-DMSO) δ 10.28 (s, 1H), 8.64 (m, 1H), 8.60 (s, 1H), 7.65 (in, 2H), 7.18 (t, 2H), 4.09 (q, 2H), 3.98 (s, 2H), 3.62 (m, 2H), 2.98 (m, 2H), 1.17 (t, 3H).

G. [4-[2-(4-Azidobenzoylamino)ethylamino]-5-(4-fluorophenylcarbamoyl)pyrimidin-2-ylsulfanyl]acetic acid ethyl ester 4-Azidobenzoyl chloride (67 mg, 0.37 mmol) was added to a solution of [4-(2-aminoethylamino)-5-(4-fluorophenylcarbamoyl)pyrimidin-2-ylsulfanyl]acetic acid ethyl ester (145 mg, 0.37 mmol) in DMF (2.0 mL). DIPEA (100 μL, 0.55 mmol, 1.5 eq) was then added to the reaction mixture and the acylation was allowed to proceed overnight at ambient temperature. The reaction mixture was concentrated by rotary evaporation and purified using flash chromatography (4 g silica gel, 10 mL/min flow rate) to yield the titled product (31 mg, 16%) as a clear glass. $^1$H NMR: (d$_6$-DMSO) δ 10.23 (s, 1H), 8.67 (m, 1H), 8.55 (s, 1H), 7.81 (d, 2H), 7.62 (m, 2H), 7.13 (m, 3H), 4.07 (q, 2H), 3.97 (s, 2H), 3.60 (m, 2H), 3.42 (m, 2H), 1.14 (t, 3H); HPLC: R$_t$=4.36 min; MS (ESI): m/z 537.31 (M–H)⁻; IR (KBr): 2126 cm$^{-1}$.

H. [4-[2-(4-Azidobenzoylamino)ethylamino]-5-(4-fluorophenylcarbamoyl)pyrimidin-2-ylsulfanyl]acetic acid 1 M NaOH (0.5 mL, 0.5 mmol) was added to a solution of [4-[2-(4-Azido-benzoylamino)-ethylamino]-5-(4-fluorophenylcarbamoyl)pyrimidin-2-ylsulfanyl]acetic acid ethyl ester (8 mg, 0.015 mmol) in THF (0.5 mL) at ambient temperature. The reaction was stirred for 1 h, then acidified with 1 N HCl to pH 3. The reaction mixture was concentrated by rotary evaporation, and the resulting solid was filtered, washed with water and dried to yield the titled product (4 mg, 53%) as a white solid. $^1$H NMR: (d$_6$-DMSO) δ 10.22 (s, 1H), 8.63 (m, 1H), 8.56 (s, 1H), 7.82 (d, 2H), 7.60 (m, 2H), 7.13 (m, 3H), 3.89 (s, 2H), 3.62 (m, 2H), 3.34 (m, 2H); HPLC: R$_t$=4.13 min; MS (ESI): m/z 509.07 (M–H)⁻.

I. 4-[4-(4-Bromophenyl)-4-hydroxypiperidin-1-yl]-2-methylsulfanylpyrimidine-5-carboxylic acid (4-fluorophenyl)amide To a mixture of 4-chloro-2-methylsulfanylpyrimidine-5-carboxylic acid (4-fluorophenyl)amide (2.0 g, 6.7 mmol) in methanol (60 mL) was added 4-bromophenylpiperidinol (2.1 g, 2.39 mmol). After 10 min, the mixture was poured into ice water and the resulting solids were collected by filtration. The filtrate was washed from the filter with ethyl acetate and the resulting solution was dried over magnesium sulfate. Filtration and concentration gave the titled compound as a white solid (2.83 g, 5.48 mmol, 78%). $^1$H NMR (300 MHz, DMSO-d$_6$) δ 10.55 (s, 1H), 8.20 (s, 1H), 7.63 (m, 2H), 7.48 (d, 2H), 7.37 (d, 2H), 4.25 (m, 2H), 3.39 (m, 2H), 1.92 (m, 2H),1.58 (m, 2H); MS (EI) m/z 514.97 (M–H)⁻.

J. [4-[4-(4-Bromophenyl)-4-hydroxypiperidin-1-yl]-5-(4-fluorophenylcarbamoyl)pyrimidin-2-yloxy] acetic acid methyl ester To a solution of 4-[4-(4-bromophenyl)-4-hydroxy-piperidin-1-yl]-2-methylsulfanylpyrimidine-5-carboxylic acid (4-fluorophenyl)amide (700 mg, 1.35 mmol) in acetone (50 mL) was added m-CPBA (330 mg, 1.49 mmol) and the mixture was stirred for 12 h. The mixture was concentrated under reduced pressure and the intermediate product was isolated by trituration from a mixture of hexanes and dichloromethane (1:1, 25mL). This afforded 534 mg of the intermediate product as a mixture of sulfoxide and sulfone. Said intermediate product was used hereinafter without further purification. To a solution of the sulfone/sulfoxide mixture (150 mg, 0.28 mmol) in THF (10 mL) was added DBU (200 mL) followed by methyl glycolate (50 mg, 0.56 mmol). The mixture was heated at reflux for 12 h. The mixture was poured into water and extracted with ethyl acetate (3×25 mL). The combined extracts were washed with water and brine and were dried over magnesium sulfate. Filtration and concentration afforded a white solid which was purified via recrystallization from hexane and dichloromethane (10:1). The afforded 125 mg of the titled product.

K. The following compounds were synthesized in a manner similar to
[4-[4-(4-bromophenyl)-4-hydroxypiperidin-1-yl]-5-(4-fluorophenylcarbamoyl)pyrimidin-2-yloxy]acetic acid methyl ester as described above:
[4-[4-(4-bromophenyl)-4-hydroxypiperidin-1-yl]-5-(4-fluorophenylcarbamoyl)pyrimidin-2-yloxy]acetic acid benzyl ester; and
[4-[4-(4-bromophenyl)-4-hydroxypiperidin-1-yl]-5-(4-fluorophenylcarbamoyl)pyrimidin-2-ylsulfanyl]acetic acid methyl ester.

L. 4-(1,1-Dioxotetrahydrothiophen-3-ylamino)-2-methylsulfanylpyrimidine-5-carboxylic acid (4-fluorophenyl)amide To a suspension of 3-amino-1,1-dioxotetrahydrothiophene (345 mg, 2.01 mmol) in methanol (5 mL) was added DIPEA (350 µL) followed by 4-chloro-2-methylsulfanylpyrimidine-5-carboxylic acid (4-fluorophenyl)amide (200 mg, 0.67 mmol). The mixture was allowed to stir for 16 h. The resulting mixture was poured into ice-water and the resulting solids were collected by filtration. The solids were washed with ethyl acetate and hexanes and were dried. This afforded 147 mg (0.37 mmol, 55% yield) of the titled product as a solid. $^1$H NMR (300 MHz, DMSO-$d_6$) δ 10.25 (s, 1H), 8.78 (d, 1H), 8.65 (s, 1H), 7.65 (m, 2H), 7.18 (m, 2H), 4.87 (m, 1H), 3.52 (m, 1H), 3.35–3.04 (m, 3H), 2.50, M, 1H), 2.22 (m, 1H); MS (EI) m/z 395.05 (M–H)⁻.

M. 2-Methylsulfanyl-4-(2-(phenylamino)phenylamino)pyrimidine-5-carboxylic acid (4-fluorophenyl)amide To a mixture of 4-chloro-2-methylsulfanylpyrimidine-5-carboxylic acid (4-fluorophenyl)amide (100 mg, 0.34 mmol) in dichloromethane (10 mL) was added N-phenyl-benzene-1,2-diamine (148 mg, 0.4 mmol) followed by N-methylmorpholine-bound resin (300 mg). The mixture was stirred at an ambient temperature for 16 h and was then heated at reflux for an additional 2 h. Methanol (5 mL) was added and the mixture was stirred at an ambient temperature for 40 h. The mixture was filtered through a plug of celite and the filter plug was washed with hot ethyl acetate (25 mL). The resulting solution was treated with hexanes to precipitate 70 mg (0.16 mmol, 47% yield) of the titled compound as a purple-red solid. $^1$H NMR (300 MHz, DMSO-$d_6$) δ 10.64 (s, 1H), 10.29 (s, 1H), 8.74 (s, 1H), 8.10 (m, 1H), 7.58 (m, 3H), 7.25–7.05 (m, 7H), 6.79–6.679(m, 3H), 2.5(s, 3H); MS (EI) m/z 444.05 (M–H)⁻.

N. 4-(3-Hydroxyphenylamino)-2-methylsulfanylpyrimidine-5-carboxylic acid (4-fluorophenyl)amide The titled compound was synthesized in a manner similar to that described above. MS (EI) m/z 369.05 (M–H)⁻.

O. 4-(2-hydroxy-2-phenylethylamino)-2-methylsulfanylpyrimidine-5-carboxylic acid (4-fluorophenyl) amide To a solution of 2-amino-1-phenyl-ethanol (140 mg, 1.01 mmol) in methanol (5 mL) was added 4-chloro-2-methylsulfanylpyrimidine-5-carboxylic acid (4-fluorophenyl) amide (100 mg, 0.34 mmol). The mixture was stirred for 16 h at an ambient temperature and the resulting mixture was poured into water. Solids were collected by filtration and were dried in vacuo to afford 103.7 mg (0.26 mmol, 78% yield) of the titled compound as a solid. $^1$H NMR (300 MHz, DMSO-$d_6$) δ 10.22(s, 1H), 8.85 (m, 1H), 8.60 (s, 1H), 7.65(m, 2H), 7.40–7.05 (m, 7H), 5.67 (m, 1H), 4.78 (m, 1H), 3.78 (m, 1H), 3.41 (m, 1H), 2.44 (s, 31H); MS (EI) m/z 397.18 (M–H)⁻.

P. The following compounds were synthesized in a manner similar to that described above:
4-(2-Hydroxy-phenylamino)-2-methylsulfanylpyrimidine-5-carboxylic acid (4-fluorophenyl)amide). MS (EI) m/z 369.22 (M–H)⁻.
4-(2-Hydroxy-1-phenyl-ethylamino)-2-methylsulfanylpyrimidine-5-carboxylic acid (4-fluorophenyl)amide. MS (EI) m/z 397.25 (M–H)⁻.

EXAMPLE 11

Pharmaceutical Compositions

This example illustrates the preparation of representative pharmaceutical compositions for oral administration containing a compound of the invention, or a pharmaceutically acceptable salt thereof:

| A. | |
|---|---|
| Ingredients | % wt./wt. |
| Compound of the invention | 20.0% |
| Lactose | 79.5% |
| Magnesium stearate | 0.5% |

The above ingredients are mixed and dispensed into hard-shell gelatin capsules containing 100 mg each, one capsule would approximate a total daily dosage.

| B. | |
|---|---|
| Ingredients | % wt./wt. |
| Compound of the invention | 20.0% |
| Magnesium stearate | 0.9% |
| Starch | 8.6% |
| Lactose | 69.6% |
| PVP (polyvinylpyrrolidine) | 0.9% |

The above ingredients with the exception of the magnesium stearate are combined and granulated using water as a granulating liquid. The formulation is then dried, mixed with the magnesium stearate and formed into tablets with an appropriate tableting machine.

| C. | |
|---|---|
| Ingredients | |
| Compound of the invention | 0.1 g |
| Propylene glycol | 20.0 g |
| Polyethylene glycol 400 | 20.0 g |
| Polysorbate 80 | 1.0 g |
| Water | q.s. 100 mL |

The compound of the invention is dissolved in propylene glycol, polyethylene glycol 400 and polysorbate 80. A sufficient quantity of water is then added with stirring to provide 100 mL of the solution which is filtered and bottled.

| D. | |
|---|---|
| Ingredients | % wt./wt. |
| Compound of the invention | 20.0% |
| Peanut Oil | 78.0% |
| Span 60 | 2.0% |

The above ingredients are melted, mixed and filled into soft elastic capsules.

| E. | |
|---|---|
| Ingredients | % wt./wt. |
| Compound of the invention | 1.0% |
| Methyl or carboxymethyl cellulose | 2.0% |
| 0.9% saline | q.s. 100 mL |

The compound of the invention is dissolved in the cellulose/saline solution, filtered and bottled for use.

EXAMPLE 12

Pharmaceutical Compositions

This example illustrates the preparation of a representative pharmaceutical formulation for parenteral administration containing a compound of the invention, or a pharmaceutically acceptable salt thereof:

| Ingredients | |
|---|---|
| Compound of the invention | 0.02 g |
| Propylene glycol | 20.0 g |
| Polyethylene glycol 400 | 20.0 g |
| Polysorbate 80 | 1.0 g |
| 0.9% Saline solution | q.s. 100 mL |

The compound of the invention is dissolved in propylene glycol, polyethylene glycol 400 and polysorbate 80. A sufficient quantity of 0.9% saline solution is then added with stirring to provide 100 mL of the I.V. solution which is filtered through a 0.2 m membrane filter and packaged under sterile conditions.

This example also illustrates the preparation of a representative pharmaceutical composition in suppository form containing a compound of the invention, or a pharmaceutically acceptable salt thereof:

| Ingredients | % wt./wt. |
|---|---|
| Compound of the invention | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

EXAMPLE 13

Pharmaceutical Compositions

This example illustrates the preparation of a representative pharmaceutical formulation for insufflation containing a compound of the invention, or a pharmaceutically acceptable salt thereof:

| Ingredients | % wt./wt. |
|---|---|
| Micronized compound of the invention | 1.0% |
| Micronized lactose | 99.0% |

The ingredients are milled, mixed, and packaged in an insufflator equipped with a dosing pump.

EXAMPLE 14

Pharmaceutical Compositions

This example illustrates the preparation of a representative pharmaceutical formulation in nebulized form containing a compound of the invention, or a pharmaceutically acceptable salt thereof:

| Ingredients | % wt./wt. |
|---|---|
| Compound of the invention | 0.005% |
| Water | 89.995% |
| Ethanol | 10.000% |

The compound of the invention is dissolved in ethanol and blended with water. The formulation is then packaged in a nebulizer equipped with a dosing pump.

EXAMPLE 15

Pharmaceutical Compositions

This example illustrates the preparation of a representative pharmaceutical formulation in aerosol form containing a compound of the invention, or a pharmaceutically acceptable salt thereof:

| Ingredients | % wt./wt. |
|---|---|
| Compound of the invention | 0.10% |
| Propellant 11/12 | 98.90% |
| Oleic acid | 1.00% |

The compound of the invention is dispersed in oleic acid and the propellants. The resulting mixture is then poured into an aerosol container fitted with a metering valve.

EXAMPLE 16

In Vitro Assays

The IL-8 and GRO-α chemokine inhibitory effects of compounds of the invention were determined by the following in vitro assays.

Preparation of PMNs:

Peripheral blood from healthy human volunteers was collected into heparin, diluted in an equal volume of PBS, layered over Ficoll-Paque Plus (Pharmacia Biotech, Uppsala, Sweden), and spun at 400×g for 30 min. The PMN rich fraction was removed and residual erythrocytes were lysed with hypotonic saline. The polymorphonuclear neutrophils (PMNs) were washed once with assay buffer (Dulbecco's PBS containing divalent cations and 0.1% endotoxin-free BSA), and resuspended at 1 E7 cells/mL in the same buffer. PMNs were loaded with 5 μM calcein AM (Molecular Probes, Eugene, Oreg.), washed twice and resuspended in assay buffer.

Chemotaxis Assay:

Chemotaxis assays with compounds of the invention were generally performed according to the method described by Frevert et al., J. Immunol. Meth. (1998), Vol. 213, pp. 41–52 using either GRO-α or IL-8 as summarized below.

Growth Related Oncogene α (GRO-α) driven chemotaxis assays were performed according to the following protocol: The lower chambers of a ChemoTx plate (Neuro Probe, Gaithersburg, Md.) were filled with 29 μL of 50 nM GRO-α (PeproTech, Rocky Hill, N.J.) and a compound of the invention. The empty upper chambers were affixed to the lower (plate), and 25 μL of PMN suspension (3E6 cells/mL), without (control) or with 0.04–40 μM of a compound of the invention, preincubated for 30 minutes, was added to the upper wells. The compounds of the invention were dissolved in DMSO (100%) at 20 mM and diluted in assay buffer to the desired concentrations; final DMSO concentration was 0.2%. Neutrophil migration proceeded for 40 minutes at 37° C. in a humidified incubator with 5% CO2. After removing nonmigrated cells from the top of the plate, migrated cells were quantified by reading fluorescence on a Wallac Victor.

Maximum chemotactic response was determined by cells to which no compound of the invention was added (positive control), whereas the negative control (unstimulated) was defined by the absence of chemokine in the lower chamber. The ratio of the positive to negative controls represents the chemotactic index of the cells.

The compounds of the invention, when tested in this assay, demonstrated the ability to prevent GRO-α driven chemotaxis of neutrophils.

Binding Assays:

[125I] IL-8 (human recombinant) was obtained from NEN Life Science Products, Inc., Boston, Mass., with specific activity of 2200 Ci/mmol. Recombinant human IL-8 was obtained from R&D Systems, Minneapolis, Minn. IL-8 type B receptor membranes were prepared from human Sf9 cells co-expressed with Gαi3β1γ2proteins by BioSignal™, Montreal, Canada. Wheat Germ Agglutinin Scintillation Proximity Assay Beads were obtained from Amersham Pharmacia Biotech, Piscataway, N.J. All assays were performed in a 96-well, solvent resistant, white PicoPlate obtained from Packard Instruments. Each reaction mixture contained [125I] IL-8 (0.16 nM), 5 μg/well IL-8RB and 1 mg/well WGA-SPA beads in 25 mM Hepes (pH 7.4), containing 2 mM CaCl2, 1 mM MgCl2, 0.1% BSA and 0.03% CHAPS. In addition, the compound of the invention was added which had been pre-dissolved in DMSO so as to reach a final concentration of between 0.01 nM and 80 μM, with a maximum final DMSO concentration of 1%. Non-specific binding was defined by the presence of 8–16 nM unlabelled IL-8. The assay was initiated by the addition of WGA-SPA beads in 25 mM Hepes (pH 7.4) containing 2 mM CaCl2 and 1 mM MgCl2. After 4–6 hours of gentle agitation at room temperature, the plate was counted on the Packard TopCount liquid scintillation counter.

The compounds of the invention, when tested in this assay, demonstrated the ability to inhibit the binding of IL-8 to its receptor, IL-8RB.

EXAMPLE 17

In Vitro Assays

Compounds of the invention were tested in the following biological assays to determine their binding affinity to other G-protein-coupled seven transmembrane receptors.

CCR5 Assay (Chemokine CCR5 (Human)):

This assay measures the binding of [125I]MIP-1β to human chemokine CCR5 receptors. See Samson, M., et al., J. Biol. Chem. (1997), Vol. 272, pp. 24934–24941. In brief, CHO-K1-P242-CCR5 cells stably transfected with a plasmid encoding the human chemokine CCR5 receptor were used to prepare membranes in modified HEPES buffer at pH 7.4 using standard techniques. A 1 μg aliquot was incubated with 0.1 nM [125I]MIP-1β for 120 minutes at 25° C. Non-specific binding was estimated in the presence of 0.1 μM MIP-1β. Membranes were filtered and washed 3 times and filters were counted to determine [125I]MIP-1β specifically bound. Compounds were screened at 20 μM.

CXCR1 Assay (Chemokine CXCR1/Interleukin IL-8a (Human)):

This assay measures binding of [125I]Interleukin-8 to human CXCR1 (ILR8A) receptors. See Ahuja, S. K. and Murphy, P. M. J. Biol. Chem. (1996), Vol. 271, pp. 20545–20550 for details. In brief, CHO cells stably transfected with a plasmid encoding the human CXCR1 (IL8RA) chemokine receptor were used to prepare membranes in modified HEPES pH 7.4 buffer using standard techniques. A 5 μg aliquot of membrane was incubated with 8 pM [125I] Interleukin-8 for 60 minutes at room temperature. Non-specific binding was estimated in the presence of 10 nM interleukin-8. Membranes were filtered and washed 3 times and the filters were counted to determine [125I]Interleukin-8 specifically bound. Compounds were screened at 20 μM.

NPY1 Assay (Neuropeptide Y1 (Human)):

This assay measures the binding of [125I]Peptide YY (PYY) to human neuropeptide Y1 (NPY1) receptors. See Fuhlendorff, J., et al., Proc. Natl. Acad. Sci. USA (1990), Vol. 87, pp. 182–186 and Sheikh, S. P., et al., J. Biol. Chem. (1989), Vol. 264, pp. 6648–6654. In brief, SK-N-MC (human neuroblastoma) cells were used in modified HBSS pH 7.4 buffer using standard techniques. The cells (106) were incubated with 12.5 pM [125I]PYY for 45 minutes at 25° C. Non-specific binding was estimated in the presence of 0.1 µM NPY (human, rat). Cells were centrifuged and pellets were counted to determine [125I]PYY specifically bound. Compounds were screened at 20 µM.

Somatostatin Assay:

This assay measures binding of [125I]tyr1 somatostatin to somatostatin receptors. See Thermos, K. and Reisine, T., Mol. Pharmacol. (1988), Vol. 33, pp. 370–377, 1988, and Srikant, C. B. and Heisler, S., Endocrinology (1985), Vol. 117, pp. 271–278, 1985. In brief, AtT-20 (mouse pituitary) cells were used to prepare membranes in modified Tris-HCl pH 7.5 buffer using standard techniques. A 200 µg aliquot of membrane was incubated with 0.04 nM [125I]tyr1 Somatostatin for 60 minutes at 25° C. Non-specific binding was estimated in the presence of 1 µM somatostatin-14. Membranes were filtered and washed 3 times and the filters were counted to determine [$^{125}$I]tyr1 somatostatin specifically bound.

The compounds of the invention, when tested in the above-described assays, demonstrated minimum binding affinity to other G-protein-coupled seven transmembrane receptors.

EXAMPLE 18

In Vitro Assays

Compounds of the invention were tested in the following biological assay to determine their binding affinity to the CXCR2 receptor.

CXCR2 Assay (Chemokine CXCR2/Interleukin IL-8b (Human)):

This assay measures binding of [125I]Interleukin-8 to human CXCR2 (IL8RB) receptors. See Ahuja, et al., supra. In brief, CHO cells stably transfected with a plasmid encoding the human CXCR2 (IL8RB) chemokine receptor were used to prepare membranes in modified HEPES pH 7.4 buffer using standard techniques. A 2 µg aliquot of membrane was incubated with 15 pM [125I]Interleukin-8 for 60 minutes at room temperature. Non-specific binding was estimated in the presence of 10 nM interleukin-8. Membranes were filtered and washed 3 times and the filters were counted to determine [125I]Interleukin-8 specifically bound. Compounds were screened at 20 µM.

The compounds of the invention, when tested in the above-described assay, demonstrated binding affinity to the CXCR2 receptor.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound of formula (Ia):

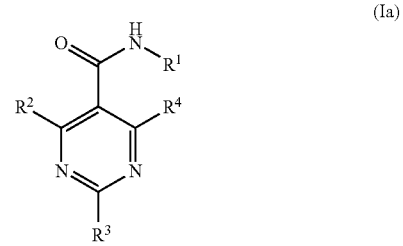

wherein, independently at each occurrence:
$R^1$ is selected from aralkyl and aryl;
$R^2$ is —N($R^5$)$R^6$;
$R^3$ is selected from —O—$R^7$ and —S(O)$_t$—$R^7$ where t is 0 to 2;
$R^4$ is selected from hydrogen, halo, and alkyl;
$R^5$ is hydrogen;
$R^6$ is hydrogen; and
$R^7$ is selected from aryl, aralkyl, heteroalkyl, heterocyclyl and heterocyclylalkyl;
provided, however, that $R^1$ can not be phenyl substituted at the 2-position by carboxy or alkoxycarbonyl when $R^2$ and $R^4$ are both hydrogen and $R^3$ is —O—$R^7$ where $R^7$ is pyridinyl or 4-methoxyphenyl, or when $R^2$ and $R^4$ are both hydrogen and $R^3$ is —S—$R^7$ where $R^7$ is pyridinyl;
and, provided that $R^7$ cannot be 4-t-butylphenyl, 4-fluorophenyl, or methylacetyl when $R^3$ is —O—$R^7$;
as a single stereoisomer, a mixture of individual stereoisomers, or a racemic mixture; or
pharmaceutically acceptable salts or solvates thereof.

2. The compound of claim 1 wherein $R^3$ is —S-phenyl wherein the phenyl is optionally substituted with carboxy or alkoxycarbonyl.

3. The compound of claim 1 wherein $R^3$ is selected from —O-aralkyl wherein the alkyl group of the aralkyl group is optionally substituted by one or more substituents selected from hydroxy, carboxy or alkoxycarbonyl.

4. A compound of formula (Ia) wherein:

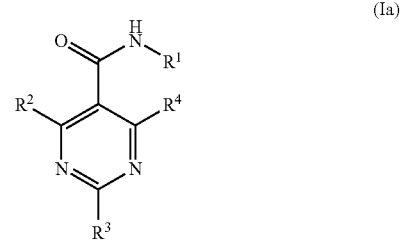

$R^1$ is phenyl or benzyl substituted by one or more substituents selected from halo, haloalkyl or haloalkoxy;
$R^2$ is selected from hydrogen and —N($R^5$)$R^6$;
$R^3$ is selected from —O—$R^7$ or —S(O)$_t$—$R^7$ where t is 0 to 2;
$R^4$ is selected from hydrogen, chloro and methyl;
$R^5$ is hydrogen;
$R^6$ is selected from hydrogen, alkyl, haloalkyl, carbocyclyl, aryl, aralkyl, heteroalkyl, heterocyclyl, and heterocyclylalkyl; or R$^5$ and R$^6$, together with the nitrogen to which they are attached, form morpholinyl, piperidinyl, or pyrrolidinyl; and R$^7$ is selected from aryl, aralkyl, heteroalkyl, heterocyclyl or heterocyclylalkyl;

provided, however, that R$^7$ cannot be 4-t-butylphenyl, 4 fluorophenyl, or methylacetyl when R$^3$ is —O—R$^7$.

5. The compound of claim 4 selected from the group consisting of the following:

4-[4-(4-bromophenyl)-4-hydroxypiperidin-1-yl]-2-methylsulfanylpyrimidine-5-carboxylic acid (4-fluorophenyl)amide;

[4-[4-(4-bromophenyl)-4-hydroxypiperidin-1-yl]-5-(4-fluorophenylcarbamoyl)pyrimidin-2-yloxy]acetic acid methyl ester;

[4-[4-(4-bromophenyl)-4-hydroxypiperidin-1-yl]-5-(4-fluorophenylcarbamoyl)pyrimidin-2-yloxy]acetic acid benzyl ester;

[4-[4-(4-bromophenyl)-4-hydroxypiperidin-1-yl]-5-(4-fluorophenylcarbamoyl)pyrimidin-2-ylsulfanyl]acetic acid methyl ester;

[4-amino-5-(4-fluorophenylcarbamoyl)pyrimidin-2-ylsulfanyl]acetic acid benzyl ester;

[4-amino-5-(4-fluorophenylcarbamoyl)pyrimidin-2-ylsulfanyl]acetic acid 4-nitro-benzyl ester;

[4-amino-5-(4-fluorophenylcarbamoyl)pyrimidin-2-ylsulfanyl]acetic acid allyl ester;

[4-amino-5-(4-fluorophenylcarbamoyl)pyrimidin-2-ylsulfanyl]acetic acid;

[4-amino-5-(4-fluorophenylcarbamoyl)pyrimidin-2-ylsulfanyl]acetic acid ethyl ester;

[4-amino-5-(4-fluorophenylcarbamoyl)pyrimidin-2-ylsulfanyl]acetic acid methyl ester;

[4-amino-5-(4-fluorophenylcarbamoyl)pyrimidin-2-ylsulfanyl]acetic acid propyl ester;

[4-amino-5-(4-fluorophenylcarbamoyl)pyrimidin-2-ylsulfanyl]acetic acid 4-chloro-benzyl ester;

[4-amino-5-(4-fluorophenylcarbamoyl)pyrimidin-2-ylsulfanyl]acetic acid 2-naphthalen-1-yl-ethyl ester;

[4-amino-5-(4-fluorophenylcarbamoyl)pyrimidin-2-ylsulfanyl]acetic acid biphenyl-4-ylmethyl ester

[4-amino-5-(4-fluorophenylcarbamoyl)pyrimidin-2-ylsulfanyl]acetic acid 3,5-dimethoxy-benzyl ester;

4-{2-[4-amino-5-(4-fluorophenylcarbamoyl)pyrimidin-2-ylsulfanyl]acetoxymethyl}benzoic acid methyl ester;

[4-amino-5-(4-fluorophenylcarbamoyl)pyrimidin-2-ylsulfanyl]acetic acid pentafluorophenylmethyl ester;

[4-amino-5-(4-fluorophenylcarbamoyl)pyrimidin-2-ylsulfanyl]acetic acid 9H-fluoren-9-yl ester

[4-amino-5-(3,4-difluorobenzylcarbamoyl)pyrimidin-2-ylsulfanyl]acetic acid benzyl ester;

3-[5-(4-fluorophenylcarbamoyl)pyrimidin-2-ylsulfanyl] benzoic acid;

[5-(4-fluorophenylcarbamoyl)pyrimidin-2-yloxy]acetic acid benzyl ester;

[5-(4-fluorophenylcarbamoyl)pyrimidin-2-ylsulfanyl] acetic acid methyl ester;

[5-(4-fluorophenylcarbamoyl)pyrimidin-2-yloxy]acetic acid cyclohexyl ester;

[5-(4-fluorophenylcarbamoyl)pyrimidin-2-yloxy]acetic acid phenyl ester; and

[4-amino-5-(4-fluorophenylcarbamoyl)pyrimidin-2-ylsulfanyl]acetic acid 2-phenylethyl ester.

6. A compound of formula (Ib):

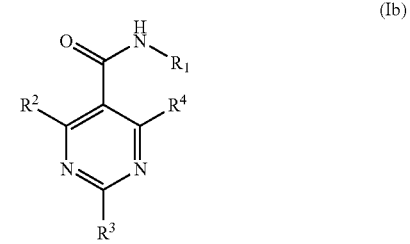

(Ib)

wherein, independently at each occurrence:

R$^1$ is selected from 4-fluorophenyl, 4-trifluoromethylphenyl, and 4-trifluoromethoxyphenyl;

R$^2$ is hydrogen;

R$^3$ is —N(R$^{10}$)R$^{11}$;

R$^4$ is hydrogen;

R$^{10}$ is selected from hydrogen and alkyl; and

R$^{11}$ is selected from carbocyclylalkyl and heteroalkyl; or

R$^{10}$ and R$^{11}$, together with the nitrogen to which they are attached, form a heterocyclyl, provided that such heterocyclyl is not imidazolin-2-onyl, phenylpiperazinyl, or 4-morpholino;

as a single stereoisomer, a mixture of individual stereoisomers, or a racemic mixture; or pharmaceutically acceptable salts or solvates thereof.

7. The compound of claim 6 wherein:

R$^1$ is 4-fluorophenyl; and

R$^{11}$ is carbocyclylalkyl.

8. The compound of claim 7 wherein:

R$^1$ is 4-fluorophenyl; and

R$^{11}$ is adamantylmethyl.

9. The compound of claim 6 wherein:

R$^1$ is 4-fluorophenyl; and

R$^{11}$ is heteroalkyl of the formula —(CH$_2$)$_m$—C(O)OR$^9$ where m is 1 to 4 and R$^9$ is hydrogen or alkyl.

10. The compound of claim 9, i.e., 3-[5-(4-fluorophenylcarbamoyl)pyrimidin-2-ylamino]propionic acid.

11. The compound of claim 6 wherein:

R$^1$ is selected from 4-fluorophenyl, 4-trifluoromethylphenyl and 4-trifluoromethoxyphenyl;

R$^2$ and R$^4$ are each hydrogen;

R$^3$ is —N(R$^{10}$)R$^{11}$;

R$^{10}$ and R$^{11}$, together with the nitrogen to which they are attached, form piperazinyl.

* * * * *